US012781166B2

(12) United States Patent

Schlack

(10) Patent No.: US 12,781,166 B2

(45) Date of Patent: Nov. 3, 2026

(54) SMART TANK FOR A BIO-PHARMA PROCESS

(71) Applicant: ESTR Biosystems GmbH, Göttingen (DE)

(72) Inventor: Stefan Schlack, Göttingen (DE)

(73) Assignee: ESTR Biosystems GmbH, Göttingen (DE)

( * ) Notice: Subject to any disclaimer, the term of this patent is extended or adjusted under 35 U.S.C. 154(b) by 816 days.

(21) Appl. No.: 18/010,080

(22) PCT Filed: Jun. 15, 2021

(86) PCT No.: PCT/EP2021/066098

§ 371 (c)(1),
(2) Date: Dec. 13, 2022

(87) PCT Pub. No.: WO2021/255020

PCT Pub. Date: Dec. 23, 2021

(65) Prior Publication Data

US 2023/0265375 A1 Aug. 24, 2023

(30) Foreign Application Priority Data

Jun. 15, 2020 (EP) .................................... 20180048

(51) Int. Cl.
*C12M 1/00* (2006.01)
*C12M 1/12* (2006.01)
(Continued)

(52) U.S. Cl.
CPC ............ *C12M 23/02* (2013.01); *C12M 23/42* (2013.01); *C12M 23/44* (2013.01); *C12M 29/04* (2013.01); *C12M 37/00* (2013.01); *C12M 41/00* (2013.01)

(58) Field of Classification Search
None
See application file for complete search history.

(56) References Cited

U.S. PATENT DOCUMENTS

2006/0196501 A1* 9/2006 Bibbo .................... C12M 23/14 128/200.23
2010/0029000 A1* 2/2010 Zhong .................... C12M 23/12 435/303.1

(Continued)

FOREIGN PATENT DOCUMENTS

CN 101406889 4/2009
CN 107002944 8/2017

(Continued)

OTHER PUBLICATIONS

Document titled "A Chicken Feed For Producing Intelligent Fermentation Tank", machine translation of CN 210261793 U provided by Clarivate Analytics, original document published Apr. 7, 2020 (Year: 2020).*

(Continued)

*Primary Examiner* — Holly Kipouros

(74) *Attorney, Agent, or Firm* — McCarter & English, LLP; Wei Song; George Blazeski

(57) ABSTRACT

The present invention relates to smart tank for a bio-pharma process line, a smart tank assembly, a method for assembling a smart tank and a system comprising multiple smart tanks. The smart tank comprises a top plate element, at least one sidewall element, and a bottom plate element, wherein the top plate element, the at least one sidewall element and the bottom plate element are arranged to form a reservoir for receiving at least one biochemical medium. The smart tank comprises further at least one channel, for guiding the at least one biochemical medium and/or an operating medium. The at least one channel extends within the top plate element and at least one of the at least one sidewall element and/or the bottom plate element.

16 Claims, 21 Drawing Sheets

(51) Int. Cl.
*C12M 1/34* (2006.01)
*C12M 3/00* (2006.01)

(56) References Cited

U.S. PATENT DOCUMENTS

| | | | | |
|---|---|---|---|---|
| 2011/0003323 | A1 | 1/2011 | Bargh | |
| 2011/0124078 | A1 | 5/2011 | Edwards et al. | |
| 2012/0177533 | A1* | 7/2012 | Lee | B01F 27/2121 422/38 |
| 2019/0194589 | A1 | 6/2019 | Gebauer et al. | |
| 2019/0376016 | A1* | 12/2019 | Lei | C12N 5/0606 |
| 2020/0255790 | A1* | 8/2020 | Veraitch | C12M 37/04 |
| 2021/0355422 | A1* | 11/2021 | Nuber | C12M 29/00 |

FOREIGN PATENT DOCUMENTS

| | | | |
|---|---|---|---|
| CN | 210261793 | U * | 4/2020 |
| DE | 102006020188 | A1 | 11/2007 |
| KR | 101937039 | B1 | 1/2019 |
| WO | WO 2016/075186 | | 5/2016 |
| WO | 2018/124888 | A1 | 7/2018 |
| WO | 2021/255018 | A1 | 12/2021 |
| WO | 2021/255038 | A1 | 12/2021 |

OTHER PUBLICATIONS

Document titled Description DE102006020188A1, machine translation of DE102006020188A1 provided by Espacenet, original document published 2007 (Year: 2007).*

Modena et al., Smart Cell Culture Systems: Integration of Sensors and Actuators into Microphysiological Systems, 2018, ACS Chem. Biol., 13, 1767-1784 (Year: 2018).*

International Search Report and Written Opinion for Application No. PCT/EP2021/066098, dated Sep. 16, 2021, 10 pages.

* cited by examiner

SMART TANK FOR A BIO-PHARMA PROCESS

CROSS REFERENCE TO RELATED APPLICATIONS

This application is a U.S. National Stage Application filed under 35 U.S.C. § 371, based on International Patent Application No. PCT/EP2021/066098, filed on Jun. 15, 2021, which claims priority to European Patent Application No. 20180048.9, filed on Jun. 15, 2020.

FIELD OF THE INVENTION

The present invention relates to a smart tank, a smart tank assembly, a smart tank system and a method for assembling a smart tank. The smart tank and/or the smart tank system may be used in a bio-pharma process, and may further be adapted for manufacturing and/or developing e.g. bio-pharmaceutical goods and/or for developing and/or testing the commercial manufacturing process of the same.

BACKGROUND ART

Bio-pharmaceutical goods, such as drugs, e.g. for cancer therapy, genetic therapy and/or cell therapy, are nowadays manufactured in so called bio-pharma process lines.

Known bio-pharma process lines are e.g. based stainless-steel tanks that are interconnected by pipes and/or the like. Those known bio-pharma process lines are difficult to maintain and to clean. Thus, so called single-use bio-pharma process lines were developed that are replaced after usage. Here, single-use containers, such as bags, serve as reservoirs for educts and/or products of the bio-pharma process line. Said bags are typically supported in rigid containers, such as stain-less steel containers, and are interconnected by hoses. For setting up a conventional single-use bio-pharma process line a complex manual assembly is required, leading to increased costs. For example, multiple bags, filters, sensors, valves, etc., have to be connected via various hoses. The complex assembly bears a significant risk for mal-function of the bio-pharma process line, due to improper or incorrect assembling.

Further, the single-use bio-pharma process lines a prone to damages as the (hose-based) connections and/or bags of the single use containers tend to leakages over the operational time. In case of leakage or mal-function, the educts and/or products of the entire bio-pharma process line can be damaged or even destroyed. Accordingly, there is a significant economic risk for the operator of the bio-pharma process line.

Still further, known single-use bio-pharma process lines typically include different materials that are in contact with the educts and/or products, thereby increasing the risk of contamination of the same. This contamination may be caused by extractables and particularly leachables initially contained in the different materials of the bio-pharma process line. Further, cell growth and/or other bio-chemical process steps may be distorted. Particularly, if pumps are used to transport the educt- and/or product-containing fluids through the bio-pharma process line, there is a risk of particle generation, due to abrasion.

Due to the complex built of the single-use bio-pharma process lines, automatization of assembling and operating the bio-pharma process lines is very difficult and expensive. Thus, in particular smaller bio-pharma process lines are oftentimes manually operated.

Further, after usage, all components of the single-use bio-pharma process line are typically discarded, as cleaning or recycling is oftentimes impossible.

In view of the above, it is an object of the present invention to provide a smart tank and a smart tank system that may be used in a bio-pharma process line and a smart tank assembly and a method for assembling a smart tank, that overcome the above-mentioned drawbacks. Further, costs and time required for developing and manufacturing bio-pharmaceutical goods shall be reduced, thereby allowing a faster time-to-market. Particularly, the smart tank and/or the smart tank system shall be adapted to be operated automatically. Further the smart tank and/or the smart tank system shall be adapted to be assembled automatically.

SUMMARY OF THE INVENTION

The object is achieved by a smart tank, a smart tank assembly, a smart tank system and a method for assembling a smart tank according to the independent claims. Further embodiments are described in the dependent claims and the following description. Parts of the description that do not fall under the scope of the claims are provided to give a better understanding of the claimed invention.

In particular, the object is achieved by a smart tank for a bio-pharma process line. The smart tank comprises a top plate element, at least one sidewall element, and a bottom plate element. The top plate element, the at least one sidewall element and the bottom plate element are arranged to form a reservoir for receiving at least one biochemical medium. The smart tank comprises further at least one channel, for guiding the at least one biochemical medium and/or an operating medium, wherein the at least one channel extends within the top plate element and at least one of the at least one sidewall element and/or the bottom plate element.

Generally, all channels and/or reservoirs of the smart tank may be configured to be self-emptying. I.e. medium that has entered the channel and/or reservoir can flow out of the respective channel and/or reservoir by gravitation.

The assembled smart tank may comprise one reservoir or multiple (at least two) reservoirs, formed by the top plate element, at least one sidewall element, and a bottom plate element. In case of multiple reservoirs, the reservoirs may be arranged serial or parallel to each other. Medium flowing through serial reservoirs flows through the single reservoirs one after another. Medium flowing through parallel reservoirs flows through the single reservoirs in a parallel fashion. Combinations of serial and parallel arrangement of the reservoirs is also possible.

The smart tank is adapted for being used in a bio-pharma process line, for manufacturing and/or developing bio-pharmaceutical goods and/or for developing and/or testing the commercial manufacturing process of these goods. Further, the smart tank may be used in other manufacturing lines and may be adapted to be operated automatically and/or manually.

The biochemical medium and/or the operating medium may be any educt or product of the process line, such as sample containing medium, cell containing medium, drug containing medium, buffer medium, acids, bases, and/or the like. The medium may comprise at least one of the following: small molecule API, antibody, drug conjugates, RNA or fragments thereof, rec proteins, viral vaccines, bacterial/microbial processes, virus like particles, viral vectors, ADC, DNA, and/or the like. Further, the operating medium may comprise heating or cooling fluids, pressurized air or gases, and/or the like. For example, in case pressurized air is used as operating medium, the operating medium may serve for driving a biochemical medium through the channel and/or into (or out of) the reservoir of the smart tank.

The biochemical medium and/or the operating medium may be provided in liquid and/or gaseous form as well as in form of solutions and/or emulsions and/or suspensions.

Particularly, the operating medium, such as pressurized air, may be used to transfer a biochemical medium to and/or out of the smart tank. Therefore, the smart tank is operable via the operating medium. For transferring a biochemical medium out of the smart tank, a positive pressure can be applied to the first smart tank, by applying operating medium to the smart tank. Thus, biochemical medium is urged out of the smart tank, e.g. towards a second smart tank and/or a filter. For transferring biochemical medium into the smart tank, a negative pressure can be established, e.g. by removing (operating) medium from the smart tank. In case pressurized air is used as operating medium, preferably sterile pressurized air is used. Sterile pressurized air can be obtained by guiding pressurized air through a respective sterile filter prior to entering the smart tank. Operating medium, such as pressurized air can be supplied to or removed from the smart tank by a respective gas inlet and/or outlet port.

The terms top plate element, side wall element and bottom plate element do not specify the orientation of the smart tank, when being assembled and in use. Rather, the assembled smart tank may be used in any orientation. Typically, the bottom plate element serves as a base and can optionally be provided on a stand for adjusting the height of the smart tank, when being in use/operation. For example, the orientation of the smart tank can be a standing orientation (i.e. the top plate element is on top), a lying orientation (i.e. a side wall element is on top), or an upside-down orientation (bottom plate element is on top).

Providing a top plate element, at least one side wall element and bottom plate element that are arranged to form a reservoir for receiving at least one biochemical medium facilitates cleaning and maintaining the smart tank after being used. Thus, the elements or at least some of the elements can be reused and/or recycled separately. Further, the smart tank—respectively the elements forming the reservoir—can be easily cleaned and sterilized prior to use.

Optionally, the at least one side wall element may be integrally formed with the top plate element or the bottom plate element. Thus, assembling the smart tank is facilitated.

The at least one channel of the smart tank is configured for guiding at least one biochemical medium and/or an operating medium. Optionally, the smart tank may comprise multiple channels, wherein each of said channels may be adapted to guide a different biochemical medium and/or an operating medium, if the smart tank is in use. The at least one channel extends within at least one of the top plate element, the at least one sidewall element and the bottom plate element. Different channels may be provided in different or same elements, so that each of the top plate element, the at least one sidewall element and/or the bottom plate element may comprise at least one (or multiple) channels.

A channel is any inner lumen that extends in the top plate element, the at least one sidewall element and/or the bottom plate element and that is adapted to guide a flow of a biochemical medium and/or an operating medium. Particularly, the channel may be integrally formed with the respective element(s). The channel may be in communication with the reservoir of the smart tank and/or may bypass the reservoir of the smart tank.

A further channel may be formed in a tube, such as a rigid tube, that can be inserted in the reservoir, e.g. through an opening in one of the top plate element, the at least one sidewall element and/or the bottom plate element. Said tube may be sealingly received in said respective opening of the top plate element, the at least one sidewall element and/or the bottom plate element. The further channel may be configured for guiding at least one biochemical medium and/or an operating medium from the outside of the smart tank into the reservoir of the smart tank.

The channel may have a diameter in the range of 0.1 to 3 inch (0.25 to 7.6 cm), preferably in the range of 0.2 to 2 inch (0.5 to 5.1 cm), more preferably in the range of 0.3 to 1.5 inch (0.75 to 3.8 cm), even more preferably in the range of 0.5 to 1 inch (1.2 to 2.5 cm) and most preferably about 0.75 inch (1.9 cm). Further, different channels may have different diameters and/or the diameter of the channel may vary. Thus, e.g. nozzles may be provided.

Particularly, a channel may extend, at least partially, in the top plate element and at least one of the at least one sidewall element and/or the bottom plate element, wherein the length of the channel is longer than the thickness of the respective top plate element, sidewall element and/or the bottom plate element. Accordingly, the medium may be guided by the channel in a direction that is different from a surface normal of a main surface of the respective top plate element, sidewall element and/or the bottom plate element.

Optionally, the medium transfer to and/or from the reservoir may be achieved exclusively by the at least one channel or multiple channels that extends in the top plate element, the at least one sidewall element and/or the bottom plate element. Thus, the at least one channel and the surface of the reservoir that are in contact with the medium, may be of the same material. Thus, the risk of contamination of the educts and/or products of a bio-pharma process line (i.e. biochemical medium and/or an operating medium) can be reduced and cell growth and/or other bio-chemical process steps are not distorted due to unfavorable combinations of different materials.

Transferring the medium using the channels allows to provide a high lot to lot consistency of the product line. This is, as in conventional fluid connections using e.g. hoses (as e.g. in conventional single use lines) lot to lot variations of the different contact materials occurs. This leads to undesired and unpredicted contamination of the transferred fluid. By transferring the medium using the channel(s) of the smart tank elements, the number of different contact materials can be reduced to a minimum and lot to lot consistency of the product line can be increased.

The at least one channel may extend in the at least one sidewall element, the top plate element and the bottom plate element. In another example, the at least one channel may extend in the top plate element and in at least one sidewall element. At least one additional channel may extend in the at least one sidewall element, the top plate element and/or the bottom plate element.

Via the at least one channel (or respectively the additional channel), a biochemical medium may be removed from a lower portion of the smart tank (e.g. via a first end of the channel, being provided in the bottom plate element or in a sidewall element in proximity to the bottom plate element) and guided to an upper portion of the smart tank (e.g. via a second end of the channel, being provided in the top plate element or in a sidewall element in proximity to the top plate element) e.g. for being transferred into a further smart tank. Accordingly, a biochemical medium may be removed from an upper portion of the smart tank (e.g. via a first end of the channel, being provided in the top plate element or in a sidewall element in proximity to the top plate element) and guided to a lower portion of the smart tank (e.g. via a second end of the channel, being provided in the bottom plate element or in a sidewall element in proximity to the bottom plate element) e.g. for being transferred into a further smart tank. Further, an operating medium, such as a heating or cooling medium may be guided within the at least one sidewall element and at least one of the top plate element and the bottom plate element, so as to provide a proper cooling/heating of the smart tank. The heating or cooling medium may be guided within the top plate element, the at least one sidewall element and/or the bottom plate element without being in contact to the reservoir. Thus, the heating or cooling medium and the bio-chemical medium are separated from each other.

Generally, the smart tank may serve as reservoir for any educt or product of the process line, such as a biochemical medium and/or an operating medium. Thus, the received medium may be stored and/or transported. Further, the smart tank may be configured to blend different mediums received in the reservoir of the smart tank. Further, the smart tank may serve as bioreactor and may support a biologically active environment. For example, a chemical process which involves organisms or biochemically active substances derived from such organisms can be carried out in said smart tank. Further, the smart tank may be designed to grow cells or tissues in the context of a cell culture. The smart tank may be used as a batch bioreactor, a fed batch bioreactor, a concentrated fed batch bioreactor, or a continuous bioreactor and/or a perfusion bioreactor. Additionally, or optionally, the smart tank may serve as filtration unit for filtering the medium received in the reservoir of the smart tank. In this case, a filter may be provided in or on the top plate element, the at least one sidewall element and/or the bottom plate element. Further, the smart tank may serve for preparing a biochemical medium, such as a buffer medium and/or for carrying out a preparative chromatography. Further, the smart tank may comprise a cross flow cassette and/or a hollow fibre module, for filtration of virus, cell harvesting and/or ultra or dia-filtration.

The reservoir of the smart tank may have a volume of at least about 10 ml, of at least about 15 ml, of at least about 20 ml, of at least about 50 ml, of at least about 100 ml, of at least about 200 ml, of at least about 250 ml, of at least about 500 ml, of at least about 11, of at least about 21, of at least about 51, of at least about 10 l, of at least about 201, of at least about 501, of at least about 100 l, of at least about 2001, of at least about 500 l, of at least about 1000 l, of at least about 2000 l, of at least about 3000 l, of at least about 4000 l, or of at least about 5000 l. Thus, bio-pharma process lines can be scaled. For example, during development smart tanks with a small volume are used. Afterwards, during manufacturing, larger smart tanks are used. Further, smart tanks of different volumes can be combined in a smart tank system of a bio-pharma process line.

The smart tank may have a height dimension, a depths dimension and a widths dimension, wherein the ratio of hight:depth:width may be of about 2:1:1. This ratio has to be shown to be preferred in case the smart tank is used as a bioreactor. Other dimensions may be chosen, depending on the desired functionality of the smart tank. For example, it is possible to provide different kinds of sidewall elements. The side wall elements may have a width in the range of 80 mm to 1500 mm, preferably in the range of 200 mm to 1200 mm, even more preferably in the range of 300 mm to 1000 mm and most preferably in the range of 450 mm to 600 mm. Further the side wall elements may have a height in the range of 150 mm to 2000 mm, preferably in the range of 200 mm to 1300 mm, even more preferably in the range of 500 mm to 1000 mm and most preferably in the range of 450 mm to 650 mm.

Thus, different dimensions and volumes can be provided, using the same top plate element and bottom plate elements. Further, different kind of top plate elements and bottom plate elements can be combined with the same kind of sidewall elements.

The at least one channel may be chosen from a group of different channel-types, comprising the following channel types: an inlet channel, an outlet channel, a bypass channel, a heating or cooling channel, a sampling channel, or the like.

An inlet channel serves for guiding a biochemical medium and/or an operating medium to the reservoir of the smart tank. The inlet channel may comprise a sparger or may be coupled to a sparger.

An outlet channel serves for removing a biochemical medium and/or an operating medium from the reservoir of the smart tank. When being connected to a further (second) smart tank, the outlet channel of a first smart tank may be connected to an inlet cannel of the second smart tank, so as to transfer medium from the reservoir of the first smart tank to a reservoir of the second smart tank.

Further, a channel may be provided that serves for transferring a retentate from e.g. a filter or a membrane back into the smart tank. This channel may be a separate retentate channel or said channel may be integrally formed with an outlet channel. For transferring a retentate back into the smart tank, a filter or membrane can be flown through with an operating fluid, in a direction opposite to the operating direction. The operating direction is the direction in which the medium flows for filtering. During filtering, permeate goes through the membrane/filter, retentate is hold back by the membrane/filter.

A further channel may be provided that serves for transferring permeate and/or filtrate back into the reservoir and/or to another smart tank. For transferring a permeate and/or filtrate back into the reservoir and/or to another smart tank, a positive pressure may be applied on a permeate side, or a filtrate side of a filter, respectively. This may be achieved by guiding an operating medium, such as pressurized (sterile) air, to the permeate side or filtrate side, respectively. The operating medium urges the permeate towards a permeate channel that may then guide the permeate/filtrate back into the reservoir of the smart tank and/or to another smart tank. The direction of flow can be controlled by opening/closing respective valves that can be associated with the respective channels.

Further channels may be provided that serve for recirculating a medium in the smart tank (recirculation channel); wetting or flushing components of the smart tank, particularly at least one filter (wetting channel, flushing fluid channel); for removing products (product channel); for providing medium (feed channel); for removing/recirculating permeate/filtrate (permeate or filtrate channel); for removing waste (waste channel); for harvesting cells (cell bleed channel); for suppling, removing and/or transferring cells (cell channel); for pressurizing at least portions of the smart tank (pressure channel) and/or for loading different solutions to the smart tank, particularly to cartridges for chromatography, i.e. for washing, cleaning, eluding (washing channel, cleaning channel, eluding channel).

A bypass-channel serves for guiding a biochemical medium and/or an operating medium, wherein the bypass-channel is not connected to the reservoir of the smart tank. Thus, a medium can bypass the smart tank without being in communication with the reservoir of the smart tank. For example, when three smart tanks are connected so that a first and a third smart tank sandwich a second smart tank, a fluid may be guided from the reservoir of the first smart tank to a reservoir of the third smart tank without passing a reservoir of the second smart tank. Optionally, the bypass-channel may be adapted to be fluidically separated from or connected to the reservoir of the smart tank. This can be achieved e.g. by a valve. Depending on the valve position (open/closed), the bypass-channel may be or may not be in communication with the reservoir of the smart tank. Thus, the flow of the medium can be controlled in that the medium bypasses the reservoir of the smart tank, or not.

For example, the bypass-channel allows to provide a biochemical medium, such as a buffer, that is used in various smart tanks of a bio-pharma process line in a large storage smart tank. Said biochemical medium can then be transferred from the storage smart tank to all smart tanks that require said medium (e.g. buffer). In case a smart tank does not require said medium, the medium can bypass the reservoir of said smart tank. Further, by providing a valve in the bypass channel, the supply of said medium can be controlled (e.g. amount and time). Further, the bypass-channel may serve for transferring a bio-chemical medium, such as a cell culture, from a first smart tank (e.g. a seed tank) in at least two subsequent smart tanks that may serve as further bioreactors. Thus, a bio-chemical medium can be guided from a single tank to multiple subsequent tanks.

A heating or cooling channel serves for guiding a tempered heating or cooling medium, for tempering the smart tank. Depending on the degree of heating/cooling, the medium received in the smart tank may evaporated or condensate. Further, the top plate element, the at least one sidewall element and/or the bottom plate element may comprise at least one longitudinal rib. The at least one longitudinal rib may protrude into the reservoir. The heating or cooling channel may be at least partially received within the at least one longitudinal rib. Thus, the efficiency of heating or cooling may be increased.

A sampling channel serves for taking a sample of biochemical medium and/or of operating medium from the reservoir of the smart tank. Thus, educts, products and intermediate products or the process line can be removed and analyzed.

The smart tank may comprise multiple channels of different channel-types and/or the same channel type. Thus, the functionality of the smart tank can be adapted to the specific needs of the respective process line.

In particular, the smart tank may be a multi-functional smart tank comprising multiple channels of different channel-types and/or the same channel type. At least one channel may be opened and closed, using e.g. a valve, a closure, or the like. Thus, depending on desired functionality a channel or multiple channels can be closed. These closed channels are not used. At least one other or multiple other channels may be opened and therefore used, thereby defining the functionality of the multi-functional smart tank.

The smart tank may comprise a heating or cooling finger that may be inserted into the smart tank through the top plate element, the at least one sidewall element, and/or the bottom plate element. The heating or cooling finger serves for guiding a tempered heating or cooling medium, for tempering the smart tank, wherein the heating or cooling medium guided by the heating or cooling finger is separated from the contents of the reservoir. Depending on the degree of heating/cooling, the medium received in the smart tank may evaporate or condensate.

The smart tank may comprise at least one port, wherein the at least one port may be associated with a respective channel. The port may be chosen from a group of port-types, comprising the following port-types: a fluid inlet port, a gas inlet port, a fluid outlet port, a gas outlet port, a cell bleed port, a tank-interconnecting port, an element-interconnecting port, a medium supply port, a medium remove port and/or the like.

The (fluid or gas) inlet port serves for providing a biochemical medium and/or an operating medium to the reservoir of the smart tank. A (fluid or gas) outlet port serves for removing a biochemical medium and/or an operating medium from the reservoir of the smart tank. A medium supply port allows to supply medium (biochemical medium and/or an operating medium) to the smart tank and a medium remove port allows to remove medium (or parts thereof) from the smart tank. The medium remove port may also serve for transferring a retentate from e.g. a filter or a membrane back into the smart tank. A tank-interconnecting port serves for coupling a channel of a first smart tank fluidically to a corresponding channel of a second smart tank, when the first smart tank is connected with the second smart tank, e.g. by using a connector means as will be described in greater detail below. A tank-interconnecting port may serve as medium supply port and/or medium remove port. A cell bleed port serves for removing cells from the reservoir. The cells may either be discarded or may be transferred to a further smart tank or other device for further processing.

The at least one port may be associated with a valve that can preferably be controlled by a handling manipulator (or multiple handling manipulators). Thus, the flow of medium from and to the smart tank can be controlled by opening/closing the valve. Particularly, the valve may be a flow control valve, that allows to adjust the flow gradually.

For example, a channel may be associated with a tank-interconnecting port and a fluid outlet port. Thus, said channel may serve for transferring a medium, such as a fluid, from the reservoir of the smart tank to a further smart tank. In case a valve is associated with the tank-interconnecting port, the flow of the transferred medium can be controlled. Alternatively, or additionally, the flow may be controlled by controlling the pressure in the associated smart tanks (positive and/or negative pressure).

The at least one port may comprise a protruding shroud that at least partially surrounds the associated channel. The shroud may be concentrically arranged around a channel end of the associated channel. Further, the at least one port may comprise a recess, that at least partially surrounds the associated channel. The recess may be concentrically arranged around a channel end of the associated channel. Said port may be adapted to be coupled to a hose element or a pipe element so as fluidically connect the smart tank with further objects in the periphery. For example, a smart tank may be integrated in a conventional bio-pharma process line.

Further, the port (e.g. a tank-interconnecting port or an element-interconnecting port) may be adapted to engage with a corresponding port (e.g. a corresponding tank-interconnecting port or an element-interconnecting port), wherein the port and the corresponding port are formed to provide a positive locking. For example, the smart tank may comprise a port on a first side and a corresponding port on a second side, wherein the first side and the second side may be opposing outer surfaces of the smart tank. This allows to couple the smart tank with a further smart tank using the port and the corresponding port and to fluidically connect the respective channels when coupling the smart tanks. Thus, a medium can be transferred from a first smart tank to a second smart tank without the use of intermediate conduit elements, such as pipes or hoses. Thereby assembling a smart tank system of e.g. a bio-pharma process line is facilitated and less prone to assembly mistakes.

Further, an element of the smart tank (top plate element, sidewall element and/or bottom plate element) may comprise a port. A further element of the smart tank (top plate element, sidewall element and/or bottom plate element) may comprise a corresponding port. This allows to couple the elements to form the reservoir of the smart tank and thereby to fluidically connect the respective channels of the elements when assembling the smart tank. Thus, a medium can be guided though a channel formed in at least two elements of the smart tank. Thereby assembling a smart tank is facilitated and less prone to assembly mistakes.

The ports may include a sealing member (e.g. flexible sealing member, such as a rubber seal, a silicon seal, a Teflon seal, or the like). Said sealing member may be a radial and/or an axial sealing. For example, the sealing member may be provided on a shroud and/or within a recess of the port. The sealing member may be provided as sealing gasket that allows to seal multiple ports of the smart tank. Further, the sealing member may be port specific and adapted to seal only a single port.

The smart tank may comprise multiple tank-interconnecting ports to provide an interconnecting interface that allows to easily couple the smart tank to a further smart tank. Further, each element of the smart tank may comprise multiple element-interconnecting ports to provide an interconnecting interface that allows to easily couple different element of the smart tank to assemble the smart tank.

The smart tank may comprise at least one filter, wherein the least one filter may be chosen from a group of filter-types, comprising the following filter-types: a pre-filter, a sterile filter, a bacterial filter, a viral filter, a *Mycoplasma* filter, an ultrafiltration filter, a diafiltration filter, a cell filter, a cell harvest filter, a fluid filter, an air filter, a gas filter, or the like. The filter may be provided within the reservoir of the smart tank. Thus, the smart tank may serve as filtration unit for filtering the medium received in the reservoir of the smart tank. The air filter may be a syringe filter. The filter may be a liquid filter. The liquid filter may serve to provide a buffer for flushing.

Further, at least one port of the smart tank may be covered by a filter. Providing a filter-covered port allows to withhold parts of the medium in the smart tank and/or prevent other parts of a medium form entering the smart tank. In case an inlet port is covered with a filter, only filtrate can enter the smart tank. In case an outlet port is covered, only the filtrate is allowed to leave the smart tank. For example, a gas inlet port may be covered with a sterile filter. Thus, sterile pressurized air can be guided into the tank and thus, medium contained in the reservoir of the smart tank can be blown out of the reservoir, e.g. for being transferred to a further smart tank.

Further, the filter covering the at least one port may be heated and/or cooled. Thus, medium entering and/or leaving the smart tank can be tempered to a desired temperature. Further, heating the filter allows to provide a hot filtration and cooling the filter allows to provide a cold filtration. Heating a filter further serves to prevent undesired condensation.

The smart tank may comprise at least one valve. The at least one valve may be associated with the at least one channel. The at least one valve may be a flow control valve, a cutoff valve, a pressure relief valve or a non-return valve, or the like. Further, a smart tank may comprise multiple valves of the same and/or of different types. Particularly, a valve may be provided at a junction of at least two channel portions. Thus, depending on the valve position, medium can be guided to different channels and/or tanks.

A flow control valve allows to control the amount of medium flowing through the channel per unit of time (e.g. flow in liters/second). The flow control valve may be configured to control the flow dynamically, to control a biochemical process in the smart tank. A cutoff valve allows to open or close the channel.

A cut off valve may be provided in a bypass-channel. Thus, the bypass-channel may be fluidically separated from the reservoir of the smart tank (valve closed) of in communication with the reservoir of the smart tank (valve open). Further a cutoff valve allows to close channels that are not used and open channels that are used in the smart tank, depending of the functionality of the smart tank.

A non-return valve may be provided in a channel to prevent medium that shall be removed from the smart tank to flow back into the smart tank. Thus, e.g. contamination of the smart tank can be prevented.

Further, a non-return valve may prevent medium that has entered the smart tank from flowing back to its origin. Thus, a smart tank can be pressurized (e.g. by pressurized air) and medium contained in the reservoir of the smart tank can be guided in a desired direction, for example for filtration purposes. Using pressurized smart tanks allows to guide the medium without using pumps. Thus, contamination of the medium and particle generation (e.g. due to abrasion) can effectively be reduced or even prevented. Further, no (expensive) pumps, such as single use pumps or pump heads, are needed, thereby reducing the costs of the smart tank and/or the smart tank system for a bio-pharma process line. Still further, avoiding pumps facilitates cleaning, maintaining and/or sterilizing the smart tank.

The at least one valve can have any suitable configuration. For example, the at least one valve can be a ball valve, a butterfly valve, a diaphragm valve, a gate valve, a needle valve, a pinch valve, or the like.

The at least one valve may be configured to be actuated manually and/or automatically. For example, the valve can be configured to be actuated mechanically, pneumatically, hydraulically, magnetically, electrically, and/or the like. Further, the at least one valve may be configured to be actuated from the outside of the smart tank, by means of an actuating means. In particular, the valve may be a mechanical valve that is configured to be actuatable from the outside of the smart tank, by means of an actuating means. The actuating means may be an actuating rod, that connects a valve closure member that is in contact with the medium with the outside of the smart tank. The actuating rod may be supported and sealed in at least one element (top plate element, sidewall element, bottom plate element) of the smart tank. For opening/closing the valve, the actuating means can be rotated or axially displaced, depending on the type of associated valve. The actuating means may be adapted to couple with an actuating mechanism, that may be part of a handling manipulator that allows automated control of the actuating means and thus of the smart tank and/or a smart tank system.

Further, the actuating means may include a magnet (permanent or electrical) that allows to actuate a respective magnetic valve from the outside of the smart tank. Providing a magnetic actuating means facilitates the sealing of the valve, as the valve closure member and the actuating means can be separated from each other, e.g. by a continuous wall portion.

Particularly, when using mechanical and/or magnetically valves it is possible to avoid electric valve components being integrated in the smart tank. Thus, recycling of the smart tank is facilitated and improved.

The valve, valve body and/or actuating means may be initially integrated in the respective element of the smart tank or may be adapted to be integrated in the respective element of the smart tank after or during assembly of the smart tank. This facilitates the assembly of the smart tank and/or a smart tank system of a bio-pharma process lines. This is, as in conventional bio-pharma process lines valves are typically provided as separate (single-use) components that have to be connected manually to other part of the process line, such as bags, and/or the like.

The smart tank may further comprise an adaptor plate element, wherein the adaptor plate element is mounted on the top plate element. The adaptor plate element may be configured to cover a filter and/or a port of the smart tank at least partially. Further, the adaptor plate element may be configured to support an actuating means of a valve.

The adaptor plate element and the top plate element may sandwich a barrier element, wherein the barrier element is part of a clean room. The clean room may be e.g. a clean room bag or tent. In this case, the adaptor plate element may be arranged outside the clean room and the top plate element (as well as the at least one sidewall element and the bottom plate element) are arranged inside the clean room.

Further, the adaptor plate element may provide access to at least one port of the smart tank, to at least one filter of the smart tank and/or to at least one actuating means of a valve of the smart tank. In case the barrier element is sandwiched between the adaptor plate element and the top plate element, the top plate element as well as the at least one sidewall element and the bottom plate element of the smart tank can be maintained in the clean room wherein access to the smart tank from the outside of the clean room is possible via the access provided by the adaptor plate element. Thus, a biochemical medium and/or an operating medium can be supplied to and/or removed from the smart tank from the outside of the clean room. Further, the at least one valve can be actuated and controlled from the outside of the clean room.

The smart tank may further comprise at least one connector means for interconnecting the smart tank (first smart tank) with a further (second) smart tank. The connector means allows a fast set up of a smart tank system, comprising several smart tanks, as the smart tanks can be interconnected by said connector means. Thus, the assembly of a bio-pharma process line is facilitated and/or speeded up. Additionally, the risk of mal-function and/or leakage due to improper assembly can be reduced. Particularly, the connector means may be adapted for automated interconnection, so that a smart tank system of a bio-pharma process line can be automated, thereby further reducing the risk of improper assembling.

The connector means may be threaded connector means such as screws and respective nuts and/or belts or straps that interconnect the first and second smart tank.

The connector means may be a latching connector means, wherein the smart tank comprises a first latching connector means for directly interconnecting the smart tank with a further smart tank, which comprises a corresponding latching connector means. The first latching connector means may be a latching arm including a latching protrusion. The latching protrusion may be adapted to latch with a corresponding latching connector means, which may be formed as latching recess.

The smart tank may alternatively or additionally comprise a second latching connector means, which is configured to latch with an inter-latching connector means, that is adapted to latch with a second latching connector means of a further smart tank, so that the smart tank can be directly interconnected with said further smart tank, via the inter-latching connector means. Said second latching connector means may include a protrusion, such as a nob, that is adapted to latch with an inter-latching connector means, having e.g. a corresponding recess to provide a positive locking. The inter-latching connector means may be a flexible inter-latching connector means, that is tensioned upon latching with the second latching connector means of the smart tank(s), thereby urging a first smart tank against a second smart tank.

The connector means may provide a fluidical connection between the first and second smart tank. For example, the connector means may be designed and shaped, so that upon latching tank-interconnecting ports of the first and the second smart tanks engage which each other so that respective channels are aligned and in (sealed) fluid communication. Thus, the assembly of a smart tank system of a bio-pharma process line can be facilitated and speeded up.

The connector means and in particular the latching connector means may be provided at the top plate element, the at least one side wall element and/or the bottom plate element. Further, the connector means may be provided in a recessed portion of top plate element, the at least one side wall element and/or the bottom plate element so as to prevent the connector means from being damaged during transport and/or storage.

Particularly, the connector means may be configured to be operated automatically and/or tool less. The connector means may provide a permanent interconnection of the smart tanks or a separable interconnection.

At least one connector means of the smart tank may be configured as a bottom drain. The bottom drain may provide a fluidical connection between the first and second smart tank and may be provided in the lower half of the first smart tank, particularly in the bottom plate element. The bottom drain may be configured so that the first smart tank is self-emptying and/or may emptied by the application of pressure.

The top plate element, the at least one sidewall element and/or the bottom plate element may be formed from a plastic material. For example, the elements may be formed from COC (cyclic olefin copolymer), COP (cyclic olefin polymer), PP (polypropylene), PC (poly carbonate), PET (polyethylene terephthalate), and/or the like. In particular, the top plate element, the at least one sidewall element and/or the bottom plate element may be formed by injection moulding, injection blow moulding, extrusion blow molding or thermoforming, wherein top plate element, the sidewall element and/or the bottom plate element may be assembled from different sub-elements. Sub-elements may be assembled by welding and/or by adhesives. Injection molded or thermoformed elements can be manufactured cost efficient and with high quality. Thus, the costs for a smart tank and/or a smart tank system for a bio-pharma process line can be reduced, compared to conventional bio-pharma process lines.

Further, the top plate element, the at least one sidewall element and/or the bottom plate, or at least sub-elements thereof, may be formed by other manufacturing methods, such as 3D-printing, or the like.

The smart tank may comprise a coating. Particularly, the inner surface of the reservoir and/or the at least one channel may be coated. Further, at least the components of the valves, ports and/or filters of the smart tank that are in contact with the biochemical and/or operating medium may be coated. The coating may be a silicon dioxide coating, a glass-based coating and/or the like. The coating reduces the number of different contact materials that are in contact with the biochemical and/or operating medium. Thus, the risk of contamination of the biochemical and/or operating medium and/or the risk of distortion of cell growth and/or other bio-chemical process steps can be reduced.

Further, the coating may form a gas barrier and/or may provide an inert inner surface of the reservoir and/or the at least one channel. The coating may be temperature resistant to allow heating and/or cooling the smart tank. Further, recycling of the smart tank can be facilitated, as the elements of the smart tank can be formed of the same (partially coated) materials. The coating can be applied during or after manufacturing of the top plate element, the at least one sidewall element and/or the bottom plate element, i.e. e.g. during injection molding and/or thermoforming.

The smart tank may be sterilizable, by means of autoclaving, ETO gas, and/or gamma radiation, prior, during or after being assembled. As the smart tank can be assembled from the elements (the top plate element, the at least one sidewall element and/or the bottom plate element), sterilization is facilitated. In case the smart tank shall be sterilized after being assembled, the ports can be used for guiding ETO gas or steam into and out of the smart tank.

The top plate element, at least one of the sidewall elements and/or the bottom plate element of the smart tank may comprise at least one assembly-connecting means and/or at least one corresponding assembly-connecting means. The assembly-connecting means and the corresponding assembly-connecting means are configured to engage with each other, so as to secure an assembly of at least two adjacent elements, chosen from the group of top plate element, one or more sidewall elements and bottom plate element.

For example, the assembly-connecting means may be a threaded member that is integrated into at least one of the elements. The threaded member may have an internal thread or an external thread and may be integrally formed with the respective element. Optionally or additionally, the threaded member may be an inlay, such as a metal inlay, that is securely held in the respective element of the smart tank. An inlay can for example be overmolded or glued into the respective element. The corresponding assembly-connecting means can be a trough opening that can be aligned with the threaded member having an inner thread. Thus, the elements can be connected and engaged by threading a screw through the through opening into the threaded member. Further, the corresponding assembly-connecting means can be a trough opening that receives a threaded member having an outer thread. Thus, the elements can be connected and engaged by threading a nut and or the like on the threaded member, thereby engaging the elements.

Further, the assembly-connecting means may be protrusions, such as bolts. The protrusions can be integrally formed with the respective element or can be an inlay. The inlay can for example be overmolded or glued into the respective element. The corresponding assembly-connecting means may be a corresponding recess. The recess may be integrally formed with the respective element or can be an inlay, such as a sleeve. The inlay can for example be overmolded or glued into the respective element. During assembly, the assembly-connecting means engage with the corresponding assembly-connecting means and provide a positive locking. The engagement of the assembly-connecting means and the corresponding assembly-connecting means may be a self-retaining engagement. The self-retaining engagement may be achieved by a retaining force provided by a flexible member that may be provided between the elements that are engaged (e.g. a top plate element and a sidewall element, two different sidewall elements and/or a bottom plate element and a sidewall element). Due to assembly, the flexible member may be compressed, thereby providing a retaining force. Particularly, the flexible member may be a sealing member that seals the reservoir formed by the elements.

The smart tank may comprise at least one sealing member for providing a sealed connection between the element (top plate element, at least one sidewall element and bottom plate element). The sealing member may be arranged circumferentially at each sidewall element, top plate element and/or bottom plate element. When the elements are assembled to form the reservoir, the sealing member may be compressed, so as to provide a retaining force that acts on the assembly-connecting means. Thereby, a self-retaining engagement may be provided.

Further, the smart tank may comprise assembly reinforcement means for reinforcing the assembly of the top plate element, at least one of the sidewall elements and/or the bottom plate element of the smart tank. The assembly reinforcement means may include a threaded means, such as a threaded rod, a strap and/or a belt. For example, at least two of the elements may comprise a through opening for receiving a threaded rod. Those elements can then be assembled by using at least one threaded member, such as a nut, that threadedly engages with the threaded rod. Further, at least one strap or belt may be wrapped around the smart tank to reinforce the assembly of the elements. Further, the assembly reinforcement means may improve the tightness of the reservoir of the smart tank. Thus, leakage can be prevented, and the assembly of the smart tank can be facilitated.

Further, a smart tank may be installed in an external frame, that serves as reinforcement means. The external frame may be configured to apply a force on the assembled smart tank, e.g. by at least one hydraulic plate, thereby reinforcing the assembly of the smart tank. Further, the external frame may be part of a guide rail system of a handling manipulator, that allows automated control of the smart tank and/or a smart tank system.

The smart tank may comprise multiple side-wall elements, wherein the top plate element, the sidewall elements and the bottom plate element are arranged to form the reservoir. This allows a small packing size of the disassembled smart tank (i.e. the smart tank assembly).

Further, at least one of the sidewall elements and in particular each one of the multiple sidewall elements may comprise a first sidewall portion and a second sidewall portion, wherein the first sidewall portion and the second sidewall portion enclose an angle $\alpha$. Providing at least one sidewall element having angled sidewall portions allows for a more stable smart tank structure, as the side wall elements are less prone to tilting. Further, the sealing of the reservoir can be improved, and the smart tank may withstand higher inner pressures.

Generally, the smart tank may be configured to withstand an inner pressure (without leakage) of at least 2 bars, or of at least 4 bars or of at least 10 bars.

The angle α may be about 90°, or about 120° or about 135°, so that the reservoir has a substantial rectangular, hexagonal or octagonal cross-section, when seen from the top plate element side. In case of a rectangular cross-section, the smart tank can be directly interconnected with up to four neighboring smart tanks. In case of a hexagonal cross-section, the smart tank can be directly interconnected with up to six neighboring smart tanks and in case of an octagonal cross-section, the smart tank can be directly interconnected with up to eight neighboring smart tanks. In a smart tank system, smart tanks of the same and/or of different configurations, such as different cross-sections can be combined. Thus, a process line, such as a bio-pharma process line, can be installed in a very small installation space. Thereby costs, such as clean room costs, can be reduced.

The first sidewall portion of the at least one sidewall element may extend laterally farther than the second sidewall portion. This allows to provide a small packaging size. Further, the inner edge formed by the first sidewall portion and the second sidewall portion, may be a rounded edge. A rounded edge prevents medium or parts thereof (such as cells) from getting stucked in the edge. The radius of the rounded edge may be at least 1/10 of the lateral length of the (shorter) sidewall portion, at least 1/5 of the lateral length of the (shorter) sidewall portion, at least 1/2 of the lateral length of the (shorter) sidewall portion, or the length of the lateral length of the (shorter) sidewall portion. Providing a radius that is about the length of the lateral length of the sidewall portion allows to provide a substantial circular inner cross section of the reservoir of the smart tank, when seen from the top plate element side. This can be desired in case the smart tank is used for stirring or blending the contained medium.

Further, the at least one the sidewall element and in particular each one of the sidewall elements may be a curved sidewall element when seen from the top plate element side, so that the reservoir has a substantial circular or oval cross-section, when seen from the top plate element side.

The smart tank may comprise multiple sidewall elements. All sidewall elements may be arranged in the same level of the smart tank. Alternatively, the side wall elements may be arranged in different levels of the smart tank. In case all sidewall elements are arranged in the same level of the smart tank, the stack of elements in the assembled smart tank is as follows: bottom plate element/side wall element/top plate element. In case the side wall elements are arranged in different levels of the smart tank, the stack of elements in the assembled smart tank may be as follows: bottom plate element/side wall element/ . . . /sidewall element/top plate element. Accordingly, in the stack at least one side wall element follows a sidewall element. This allows to form smart tanks having different volumes, using the same elements.

Any one of the top plate element, the at least one sidewall element and/or the bottom plate element may comprise at least one first channel portion and a at least one channel-connecting means being associated with a respective first channel portion. Additionally, a different one of the top plate element, the at least one sidewall element, a further side wall element and/or the bottom plate element may comprise at least one second channel portion and a at least one corresponding channel-connecting means being associated with a respective second channel portion. The channel-connecting means and the corresponding channel-connecting means may be configured to engage with each other, so as to form a fluidically sealed channel connection, between the first channel portion and the second channel portion, so as to form the at least one channel. Particularly, the element-interconnecting port and/or a corresponding element-interconnecting port (as described above) may include a channel-connecting means and/or a corresponding channel-connecting means.

The channel-connecting means may comprise a protruding shroud that at least partially surrounds the end of the associated first channel portion. The shroud may be concentrically arranged around a channel end of the associated channel portion. Further, the corresponding channel-connecting means may comprise a recess, that at least partially surrounds the end of the associated second channel portion. The recess may be concentrically arranged around the channel end of the associated second channel portion. The channel-connecting means and the corresponding channel-connecting means may be formed to provide a positive locking. For example, an element of the smart tank (top plate element, sidewall element and/or bottom plate element) may comprise a channel-connecting means. A further element of the smart tank (top plate element, sidewall element and/or bottom plate element) may comprise a corresponding channel-connecting means. This allows to couple the elements to form the reservoir of the smart tank and thereby to fluidically connect the respective channel portions of the elements to form a connected channel, when assembling the smart tank. Thus, a medium can be guided though the channel formed in at least two elements of the smart tank. Thereby assembling a smart tank is facilitated and less prone to assembly mistakes.

The channel-connecting means and/or the corresponding channel-connecting means may include a sealing member (e.g. flexible sealing member, such as a rubber seal, a silicon seal, a Teflon seal, or the like). Said sealing member may be a radial and/or an axial sealing member. For example, the sealing member may be provided on a shroud and/or within a recess of the channel-connecting means/corresponding channel-connecting means. The sealing member may be provided as sealing gasket that allows to seal multiple channel portions of the respective element. Further, the sealing member may be channel-connecting means specific and adapted to seal only a single channel portion.

The element (top plate element, sidewall element and/or bottom plate element) may comprise multiple channel-connecting means and/or the corresponding channel-connecting means to provide a channel-connecting interface that allows to easily assemble the smart tank. The channel-connecting interface may be configured to allow assembly of different elements. For example, a sidewall element may be assembled with a top plate element or a further sidewall element, using the same channel-connecting interface.

The channel-connecting means and the respective channel portions may be arranged to built a channel, that is adapted to guide a medium multiple times through an element (e.g. a side wall element) of the smart tank. This channel may be used as a heating or cooling channel and is configured to provide a uniformly tempered surface of the respective element.

The smart tank may further comprise at least one pumping means, wherein the pumping means may be separated from the reservoir and/or the at least one channel by a flexible membrane, so as to prevent direct contact between the at least one biochemical medium and the pumping means.

The smart tank may further comprise at least one stirring means, wherein the stirring means may be drivable from the outside of the smart tank. For example, the stirring means may be driven by a magnetic actuator. Using a magnetic actuator allows to drive the stirring means from the outside of the smart tank and facilitates the sealing, as the magnetic actuator can be separated from the actual stirring means, e.g. by a continuous wall portion.

Further, the stirring means may comprise an actuating rod. Said actuating rod may be supported and sealed in at least one element (top plate element, sidewall element, bottom plate element) of the smart tank. The actuating rod can be engageable with a drive mechanism, such as an electric drive mechanism, provided on the outside of the smart tank. Preferably, the actuating rod protrudes from the top plate element. The drive mechanism may be part of a handling manipulator that allows automated control of the smart tank and/or a smart tank system.

The stirring means may be supported in the smart tank by means of the actuating rod. Further, the stirring means may be supported levitatingly in the smart tank, e.g. by a magnetic bearing. For driving the stirring means, a handling manipulator may couple magnetically to said levitatingly supported stirring means from the outside of the smart tank and drive the stirring means from the outside of the smart tank.

Further, the handling manipulator may couple mechanically and/or in any other suitable way, to said stirring means from the outside of the smart tank and drive the stirring means from the outside of the smart tank.

Moreover, the at least one handling manipulator may be provided above or underneath the smart tank(s) in order to drive the stirring means.

The stirring means may comprise at least one stirring member, wherein the stirring member comprises multiple stirring blades. The stirring blades can be provided in different forms, such as in form of a Rushton stirring blade, a pitched blade, a gentle marine blade, or the like. Further, the stirring means may comprise multiple stirring members, being e.g. provided in different levels of the smart tank. Further, the stirring means may include an integrated sparger.

The stirring means may be operable in a pulsed mode. Thereby waves are created that allow to clean up a filter from a reservoir side. Further, for cleaning up a filter, a further stirring member may be provided that is adapted to rotate in close proximity to the filter. Depending on the type of filter, the reservoir side may be a permeate side or a retentate side of the filter.

The smart tank may further comprise at least one blending means, such as a fluid deflection plate, which may be integrally formed with either one of the sidewall elements, the top plate element and/or the bottom plate element. Further, the blending means may be a separate means that is provided in the reservoir of the smart tank. The at least one blending means may be associated with an inlet port of the smart tank.

The smart tank may further comprise at least one means to avoid foaming of the at least one biochemical medium and/or operating medium. The at least one means to avoid foaming may reduce the velocity, the fall height and/or the flow properties of the at least one biochemical medium and/or operating medium. The at least one means to avoid foaming may be a fluid deflection plate and/or a channel (e.g. a rigid tube) as described above. In case of being a channel, the channel opening may be directed towards one of the sidewall elements, the top plate element and/or the bottom plate element so that the biochemical medium and/or operating medium is deflected when entering the reservoir through the channel. The at least one means to avoid foaming may be integrally formed with one of the sidewall elements, the top plate element and/or the bottom plate element. Further, the at least one means to avoid foaming may be a separate means that is provided in the reservoir of the smart tank. The at least one means to avoid foaming may be associated with an inlet port of the smart tank.

The smart tank may further comprise at least one a cell-harvest-means. The cell-harvest means may include a filter and/or a filter cartridge that can be coupled or integrated in an element, particularly the bottom plate element of the smart tank. The cell-harvest-means may comprise medium remove port (also referenced as cell bleed port), for removing the medium or parts of the medium (such as cells) contained in the reservoir of the smart tank. The medium remove port may also be provided in the bottom plate element and/or the at least one side wall element. In particular, the medium remove port can be provided anywhere on a reservoir-side of a filter of the cell-harvest-means for removing retentate, such as cells, and/or on the opposite side, for removing filtrate (permeate). Further, the cell-harvest-means may include an (operating) medium supply port, that allows to rinse a filter of the cell-harvest-means.

Further, the smart tank may be associated with at least one magnet, wherein the at least one magnet may be used for cell selection, cell activation, transduction and/or expansion. The at least one magnet may be arranged directly on the top plate element, the at least one sidewall element and/or the bottom plate element. The at least one manipulator may be adapted to arrange and/or remove the at least one magnet.

The operating medium supply port may be provided on the permeate side of the filter, or a filtrate side, respectively. Thus, when positive pressure (gaseous or fluidic) is applied on the permeate/filtrate side of the filter, e.g. via the (operating) medium supply port, the retained portion of the feed or retentate can be transferred back into the smart tank, out of the medium remove port and/or out of a waste port. Further, for transferring retentate back into the smart tank and/or out of the medium remove port a negative pressure can be applied on the retentate side of the filter.

Applying positive pressure on the permeate/filtrate side of the filter (preferably by providing a pressurized operating medium) and/or negative pressure on a retentate/upstream side of the filter, allows to flush the filter. Thus, a blocked filter, e.g. a cell filter, can be blown out.

Additionally, applying positive pressure (gaseous or fluidic) on the permeate side of the filter or a filtrate side, respectively, e.g. via the (operating) medium supply port, permeate/filtrate can be urged into a permeate channel or a respective filtrate channel. Thus, permeate/filtrate can be guided back into the reservoir and/or to a further smart tank. Preferably, positive pressure is applied by providing sterile pressurized air on the permeate side or the filtrate side, respectively.

The smart tank may further comprise at least one cartridge for chromatography, so as to allow carrying out a preparative chromatography. Further, the smart tank may comprise at least one resin means, a membrane absorber, and/or the like. The smart tank may further comprise at least one cross-flow cassette, so as to allow carrying out crossflow filtration or tangential flow filtration within the smart tank.

The smart tank may further comprise at least one hollow-fibre means for cell harvesting, dia-filtration, micro-filtration, ultra-filtration, and/or the like. The hollow-fibre means may be provided in a cartridge that can be integrated in the reservoir of the smart tank or that can be arranged outside of the reservoir of the smart tank. For example, the hollow-fibre means may be coupled to at least one of the elements of the smart tanks, using respective ports. Further, the smart tank may comprise multiple hollow-fibre means. Particularly, a smart tank may be used for increasing the cell concentration of a cell containing solution, e.g. by filtering the solvent. This allows to harvest cultivated cells.

The at least one sidewall element and/or the bottom plate element may be integrally formed with either one of the above-mentioned filter, cell-harvest-means, cartridge for chromatography, cross-flow-cassette, resin means, hollow-fibre means, and/or any other fluid storing or guiding component.

Particularly, any of one of the above-mentioned filter, cell-harvest-means, cartridge for chromatography, cross-flow-cassette, resin means, hollow-fibre means, and or any other fluid storing or guiding component may include a capsule, wherein the capsule houses the respective filter, means, cassette, and/or component. Further, the capsule and at least one of the sidewall elements and/or the bottom plate element may be integrally formed, wherein the at least one channel of the smart tank may extend within the capsule (i.e. at least one of the sidewall elements and/or the bottom plate element). Alternatively, the capsule may be connected to at least one of the sidewall elements, the top plate element and/or the bottom plate element. This connection may be permanent or reversible.

The smart tank may further comprise at least one a rupture disc. The rupture disk may be formed of different materials, such as stainless steel, graphite, silicon, plastics, and/or the like. The rupture disc may be arranged to block e.g. an outlet port, or a medium remove port of the smart tank. In case the pressure inside the reservoir exceeds a predefined threshold (e.g. due to a blocked filter), the rupture disc ruptures and medium can be guided out of the reservoir via the respective port, without damaging the smart tank. Additionally, or alternatively a pressure relief valve may be provided that allows for releasing excess pressure from the reservoir of the smart tank.

The smart tank may further comprise at least one bag, wherein the bag may line the inner wall of the reservoir. Thus, the reservoir of the smart tank can easily be prepared for receiving further fluids, e.g. by exchanging the bag.

The smart tank may be connectable to at least one sensor or a sensor module, comprising multiple sensors, wherein the at least one sensor and the sensors of the sensor module are chosen from the group of a pH sensor, a temperature sensor, a dissolved oxygen sensor, a biomass sensor, a foam sensor, a pressure sensor, a flow sensor, an $O_2$ sensor, an $N_2$ sensor, a $CO_2$ sensor, or the like. Further, the at least one sensor may be a spectroscopy means, such as RAMAN, NIR and/or UV spectroscopy means. Further, the sensor or sensor module may be connected to the smart tank. Further, the sensor or sensor module may be a single use sensor/sensor module. Moreover, the flow sensor may be an ultrasonic sensor, which is optionally arranged at the at least one channel of the smart tank. Further, the sensor or sensor module may be cleanable and optionally sterilizable.

For measuring pressure within a smart tank and/or a channel thereof, a channel may include a flexible membrane. This membrane can be associated with a pressure sensor that is adapted for the pressure inside the tank and/or the channel. Further, the pressure within the tank and/or the channel may be measured, using a hydrophobic filter, such as a vent filter, that is installed in the top plate element. This filter can be separated from the reservoir of the tank by means of a valve. For measuring the pressure, the valve can be opened.

Being able to measure the pressure in a smart tank and/or a channel thereof, allows for leakage testing of the smart tank and/or for non-destructive integrity testing of filter(s) provided in the smart tank. Prior to testing, the smart tank is pressurized, e.g. by applying pressurized air. Subsequently pressure drop can be measured and compared to respective predefined pressure values. Thus, leakage can be detected. In case the measured pressure drop exceeds the predefined pressure values, the test is not passed. For testing integrity of a filter, all input- and output channels of the smart tank should be closed, e.g. by using respective valves. Closing the valves is preferably carried out by a handling manipulator, i.e. automatically. Further, the filter should be wetted prior to testing. Wetting the filter can be achieved by opening a wetting channel that is associated with the filter to be tested. The wetting channel may guide a buffer solution to the filter, that wets the filter. Subsequently, the tank, particularly a permeate side (filtrate side) and/or a retentate side (upstream side) of the filter, may be pressurized and pressure drop over time can be measured. For pressurizing positive and/or negative pressure may be applied so that there is a differential pressure applied on the filter. The measured pressure drop can be compared to a predefined threshold to decide, whether the integrity test is passed or not. This integrity test can be performed for every filter of the tank. Integrity can then be tested e.g. using a pressure hold test, a pressure drop test and/or a forward flow test.

For testing integrity, the following steps can be carried out:

a) The filter(s) that shall be tested is wetted with a wetting fluid, e.g. by applying a buffer solution. The buffer solution may be applied through a buffer containing cartridge or smart tank, preferably by using the handling manipulator, i.e. automatically. For wetting the filter(s) a channel that fluidically connects the buffer containing cartridge or smart tank with the smart tank that contains the filter to be tested is opened, e.g. by opening a respective valve and/or by connecting the buffer containing cartridge or smart tank to the smart tank that contains the filter to be tested. Operating the valve(s) and connecting the buffer containing cartridge may be carried out by the handling manipulator.

Further it may be monitored, whether wetting is completed. Completion of the wetting step can be detected e.g. by detecting permeate and/or filtrate that has travelled through the filter to be tested. This can be done by weighing, by providing a fluid sensor, such as a capacitive sensor, and/or the like. Additionally, or alternatively, the wetting fluid and respectively pressure, may be provided for a predetermined period of time that guarantees a proper wetting of the filter(s). Excess wetting fluid can be removed via a waste channel and e.g. guided to waste tank. Further, if needed back pressure can be applied via the valves for improving the wetting of the filter.

b) After wetting is completed, e.g. the permeate side (filtrate side) and/or a retentate side (upstream side) of the filter is pressurized, preferably by applying sterile pressurized air. Prior to pressurizing, all valves that would allow pressurized air to leave the side of the filter that is pressurized should be closed, preferably by a respective handling manipulator.

For testing membrane filters, typically the upstream side of the filter is pressurized. On the filtrate side of the filter a channel may be opened, e.g. a waste channel, preferably by actuating a respective valve. This allows pressurized air that has travelled though the filter to be removed from the filtrate side.

For testing a cross flow cassette and/or a hollow fibre module pressure may be applied on the retentate side, preferably via a retentate outlet channel of the smart tank The retentate outlet channel may be openable/closable by an associated valve. The feed channel(s) of the cross flow cassette and/or a hollow fibre module may be closed for integrity testing and the permeate channel(s) of the cross flow cassette and/or a hollow fibre module may be opened for integrity testing. On the permeate side of the filter a channel may be opened, e.g. one of the permeate channels, and connected to a waste channel, preferably by actuating a respective valve. This allows pressurized air that has travelled though the filter to be removed from the permeate side.

c) After or during pressurizing, the pressure drop over time can be measured and compared to a predetermined threshold. Preferably, measuring is started after a predefined stabilization time. In case the pressure drop exceeds the threshold, the test is not passed.

After testing, the pressurized air may be removed from the smart tank via an outlet port.

Integrity testing is extremely difficult in conventional bag-based process lines, as the bags and/or hose connections expand due to the applied pressure. And therefore, the test result is distorted. Thus, in conventional bag-based process lines expensive helium leakage tests are required. Further, helium leakage testing is complex, and typically cannot be carried for interconnected bags of a conventional bag-based process lines, or even an entire bio-pharma process line. Particularly, interconnections of bags cannot be tested. Thus, being able to use integrity testing in a readily assembled process line and/or a readily assembled smart tank significantly reduces the risk of leakage. Further, costs for operating a process line.

At least one element of the smart tank (top plate element, at least one sidewall element and/or bottom plate element) may comprise a sensor module connection portion that allows to connect the sensor or a sensor module, comprising multiple sensors to the smart tank. The sensor and/or sensor module may comprise a wired or wireless data transfer unit for transferring achieved sensor data to a control unit. Further, the sensor and/or sensor module may comprise a rechargeable battery and/or a power interface for powering the sensor and/or the sensor module. The power interface may be wired or wireless, such as an inductive or capacitive power interface. Further, the sensor and/or sensor module may be configured for multi-use. Particularly, the sensor and/or sensor module may be sterilizable.

The sensor and/or sensor module may be connected with a respective handling manipulator. The connection may be wired and/or wireless. Thereby data may be transferred between the sensor and/or sensor module and the handling manipulator. Further, with said connection, the sensor may be powered by means of the handling manipulator.

The smart tank may be free of electric or electronic parts but can be connected to the same (e.g. a sensor or a sensor module). Thus, the smart tank can be easily recycled.

Further, the smart tank may comprise at least one wheel that allows to position the smart tank prior to or after being filled. The wheel may be associated with a break to prevent the smart tank from undesired movement.

Further, the object is achieved by a smart tank assembly adapted to be assembled to a smart tank as described above. The smart tank assembly comprises at least a top plate element, at least one sidewall element, and a bottom plate element. The top plate element, the at least one sidewall element and the bottom plate element can be assembled to form a reservoir for receiving at least one biochemical medium. At least one of the top plate element, the at least one sidewall element and the bottom plate element comprises at least one channel, for guiding the at least one biochemical medium and/or an operating medium. Further, at least one of the top plate element, the at least one sidewall element and the bottom plate element may comprise at least one connector means for interconnecting the smart tank with a further smart tank, when being assembled. As the smart tank assembly is adapted to be assembled to a smart tank as described above, all advantages that are described with respect to the smart tank can be achieved with the smart tank assembly, at least when being assembled. Further, the smart tank assembly allows to transport and store a disassembled smart tank with little space requirements.

Further, the object is achieved by a smart tank system, comprising multiple smart tanks as described above. A first smart tank of the smart tank system is interconnectable with a second smart tank by the at least one connector means, when the second smart tank is arranged adjacent to the first smart tank. Further, at least one of the one or more channels of the first smart tank are fluidically connected to respective channels of the second smart tank, when the first smart tank is interconnected with the second smart tank. Thus, a process line, such as a bio-pharma process line can be set up easily and automated. Particularly, the number of hose- or pipe based fluidic connections can be significantly reduced, compared to conventional process lines.

Particularly, a first smart of the smart tank system may be directly interconnectable with a second smart tank by the at least one connector means, when the second smart tank is arranged directly adjacent to the first smart tank. Alternatively, or additionally hose-based fluid connections can be used.

Further, a height dimension of the first smart tank may be smaller than a height dimension of the second smart tank and the smart tank system may comprise at least one height compensation means that is adapted to be coupled to the first smart tank, so that the top plate element of the first smart tank is installed at substantially the same height as the top plate element of the second smart tank, when the height compensation means is coupled to the first smart tank.

Thus, all top plate elements of the smart tank system can be arranged at substantially the same height. This allows to mount respective adaptor plate element on top of the plate elements, wherein the adaptor plate elements are also arranged at substantially the same height. Thus, ports of the smart tanks, filters of the smart tanks and/or actuating means of valves of the smart tanks can be accessed and operated at substantially the same height. Thereby automated actuation and operation of the smart tank system is facilitated. Further, in case the adaptor plate element and the top plate element sandwich a barrier element that is part of a clean room, the clean room can have a substantially flat upper surface and there is no need for a complex geometry.

Still further, at least one adaptor plate may be configured to be mounted on multiple top elements of different smart tanks, thereby strengthening the interconnection of said smart tanks.

The height compensation means may comprise a platform for receiving the smart tank and a stand. The stand may be variable in height. Thus, a height compensation means may be used with different kinds of smart tanks. For example, the stand may comprise a telescope mechanism or a folding mechanism. A stand that is variable in height may be actuatable, e.g. by an electric or hydraulic drive, so as to provide an automated height variation.

Further, the stand may have a predefined height. Thus, the height compensation means is suited for one kind of smart tank. The height compensation means may be integrated in the smart tank, or may be provided as a separate device of the system.

Further, the smart tank and/or the height compensation means may comprise at least one wheel. Said at least one wheel facilitates moving the smart tank to form e.g. a smart tank system comprising multiple smart tanks. The wheel may be associated with a brake. Thus, undesired movement of the smart tank can be prevented.

Further, a volume of the first smart tank may be smaller than a volume of the second smart tank and the first smart tank may be adapted to be installed on top of the second smart tank. The first and second smart tanks may be fluidically connected, wherein the fluid connection (channel) may be controlled by a valve. The first smart tank may serve to provide an operating medium and/or a biochemical medium to the second smart tank. As the first smart tank is installed on top of the second smart tank, it is possible to transfer fluid from the first smart tank to the second smart tank by using gravitation. Thus, the use of a pump can be avoided.

Further, medium can be transferred from a first smart tank to a second smart tank by pressurizing at least one of the smart tanks. In case medium shall be transferred from the first to the second smart tank, a positive pressure can be applied to the first smart tank and/or a negative pressure can be applied to the second smart tank. Thus, medium is urged from the first smart tank towards a second smart tank. In case a filter is provided between the first smart tank and the second smart tank (e.g. in an interconnection channel, and/or in a top plate element of the second smart tank, in case the first smart tank is installed on top of the second smart tank), filtration can be controlled by controlling the pressure level in the first and/or second smart tank. A positive pressure can be established by providing (operating) medium, such as pressurized air, to the smart tank. A negative pressure can be established by removing (operating) medium from the respective smart tank. In case pressurized air is used as operating medium, preferably sterile pressurized air is used. Sterile pressurized air can be obtained by guiding pressurized air through a respective sterile filter prior to entering the smart tank.

Further, the smart tank system may comprise a connection plate element. Said connection plate element may include at least one channel and may be adapted to interconnect smart tanks that are not provided directly adjacent to each other. Using a connection plate element facilitates interconnecting spaced apart smart tanks. Those spaced apart smart tanks can e.g. sandwich one or more further smart tanks. Further, a connection plate element may be configured to multiplex or demultiplex a medium flow. For example, the connection plate element may contain a channel junction or a channel manifold. Thus, a medium received from a first smart tank can be supplied to multiple other smart tanks (multiplexing). Further, different mediums can be mixed within the connection plate element and can then be jointly supplied to a single smart tank (demultiplexing). Further, the connection plate element may be integrally formed with any one of the top-plate element, the at least one side wall element and/or the bottom plate element.

Moreover, the smart tank system may comprise an adapter. Said adapter may be adapted to interconnect the first smart tank and the second smart tank. Optionally the adapter is adapted to interconnect the first smart tank and the second smart tank by means of the at least one connector means.

The adapter may include at least one channel and at least one fluidic module. The at least one channel of the adapter may be fluidically connected to a respective channel of the first smart tank and a respective channel of the second smart tank, when the adapter interconnects the first smart tank and the second smart tank.

The at least one fluidic module may serve to filter, mix, separate and/or activate a medium flow (biochemical medium and/or operating medium). The at least one fluidic module may be at least one of the following: a crossflow cassette, a crossflow hollow fiber module, a hollow fiber filter, a resin capsule, a filter capsule, and/or a magnetic tube. It is to be understood, that the adapter may include multiple fluidic modules of the same type and/or of different types.

Further, the at least one fluidic module may be replaceable. Thus, maintenance may be facilitated. Particularly, the at least one fluidic module may be replaceable by another type of fluidic module. Thus, the functionality of the adapter may be adapted with reduced effort. Further, the at least one fluidic module may be replaceable by the same type of fluidic module. Thus, e.g. a consumed filter can be easily replaced.

Further, the adapter may be adapted to interconnect smart tanks that are not provided directly adjacent to each other. Using the adapter facilitates interconnecting spaced apart smart tanks. Those spaced apart smart tanks can e.g. sandwich one or more further smart tanks. Further, the adapter may be configured to multiplex or demultiplex a medium flow, so as the connection plate element.

The object is also achieved by a method for assembling a smart tank, wherein the method comprises the following steps: providing a top plate element, providing at least one sidewall element, providing a bottom plate element and assembling the top plate element, at least one sidewall element, and a bottom plate element to form a reservoir for receiving at least one biochemical medium.

The assembling order of the elements may vary. For example, in a first step, the side wall elements may be assembled to form a continuous side wall. Then, the bottom plate element can be assembled. To close the reservoir, subsequently, the top plate element is assembled. The assembling may be fully automated. Further, the assembling is preferably carried out in a clean room or even a sterile environment. Further parts of the smart tank (as described) above may also be assembled.

BRIEF DESCRIPTION OF THE FIGURES

In the following, the accompanying figures, that schematically show embodiments of the invention are described. Here, FIG. 1 schematically shows a smart tank assembly in a disassembled state.

DETAILED DESCRIPTION OF THE FIGURES

Figure 1:
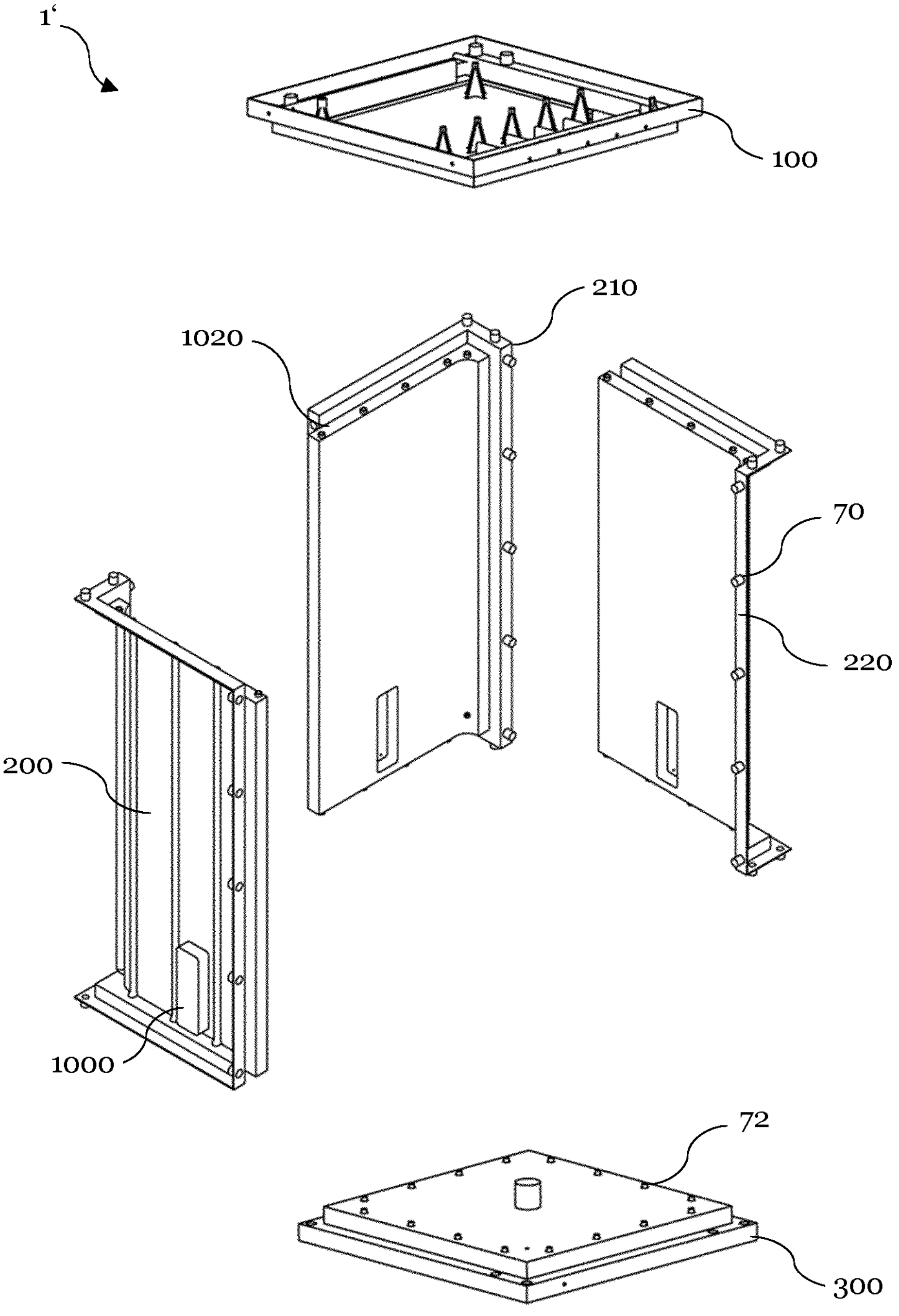

In particular, FIG. 1 schematically shows a smart tank assembly 1' in a disassembled state. The smart tank assembly 1' is adapted to be assembled to a smart tank 1 (as e.g. shown in FIG. 2). The smart tank assembly 1' comprises a top plate element 100, at least one sidewall element 200, 210, 220, and a bottom plate element 300. As depicted, the smart tank assembly 1' of FIG. 1 comprises three sidewall elements 200, 210, 220.

The top plate element 100, the sidewall elements 200, 210, 220 and the bottom plate element 300 can be assembled to form a reservoir 500 for receiving at least one biochemical and/or operating medium.

At least one of the top plate element 100, the sidewall elements 200, 210, 220 and the bottom plate element 300 comprises at least one channel, for guiding the at least one biochemical medium and/or an operating medium. The channel may be associated with a valve that allows to open/close the channel. The valve may also be a flow control valve, that allows to control the flow through the channel. The channel may further comprise a port, such as an inlet and/or outlet port.

The smart tank assembly 1' may comprise at least one sealing member 1020 for providing a sealed connection between the elements (top plate element 100, sidewall elements 200, 210, 220 and bottom plate element 300). The sealing member 1020 may be arranged circumferentially at each sidewall element 200, 210, 220, top plate element 100 and/or bottom plate element 300. When the elements are assembled to form the reservoir 500, the sealing member 1020 may be compressed, so as to provide a retaining force that acts on assembly-connecting means 70 and corresponding assembly-connecting means 72. Thereby, a self-retaining engagement may be provided.

Each of the elements (top plate element 100, sidewall elements 200, 210, 220 and bottom plate element 300) may be adapted to be provided with a sensor 1010 and/or a sensor module 1000. A sensor module 1000 may comprise multiple sensors, such as at least one of a pH sensor, a temperature sensor, a dissolved oxygen sensor, a biomass sensor, a foam sensor, a pressure sensor, a flow sensor, an O2 sensor, a N2 sensor, a CO2 sensor, and spectroscopy means, such as RAMAN, NIR and/or UV spectroscopy means. The sensor module may be connectable to the respective top plate element 100, sidewall element 200, 210, 220 and/or bottom plate element 300. The sensor module 1000 may be provided with a power source such as a rechargeable battery, that allows to operate the sensor module 1000 autonomously. Further, the sensor module 1000 may comprise a data interface, particularly a wireless data interface for transferring the measured sensor data to a respective control or storing unit.

Figure 2:
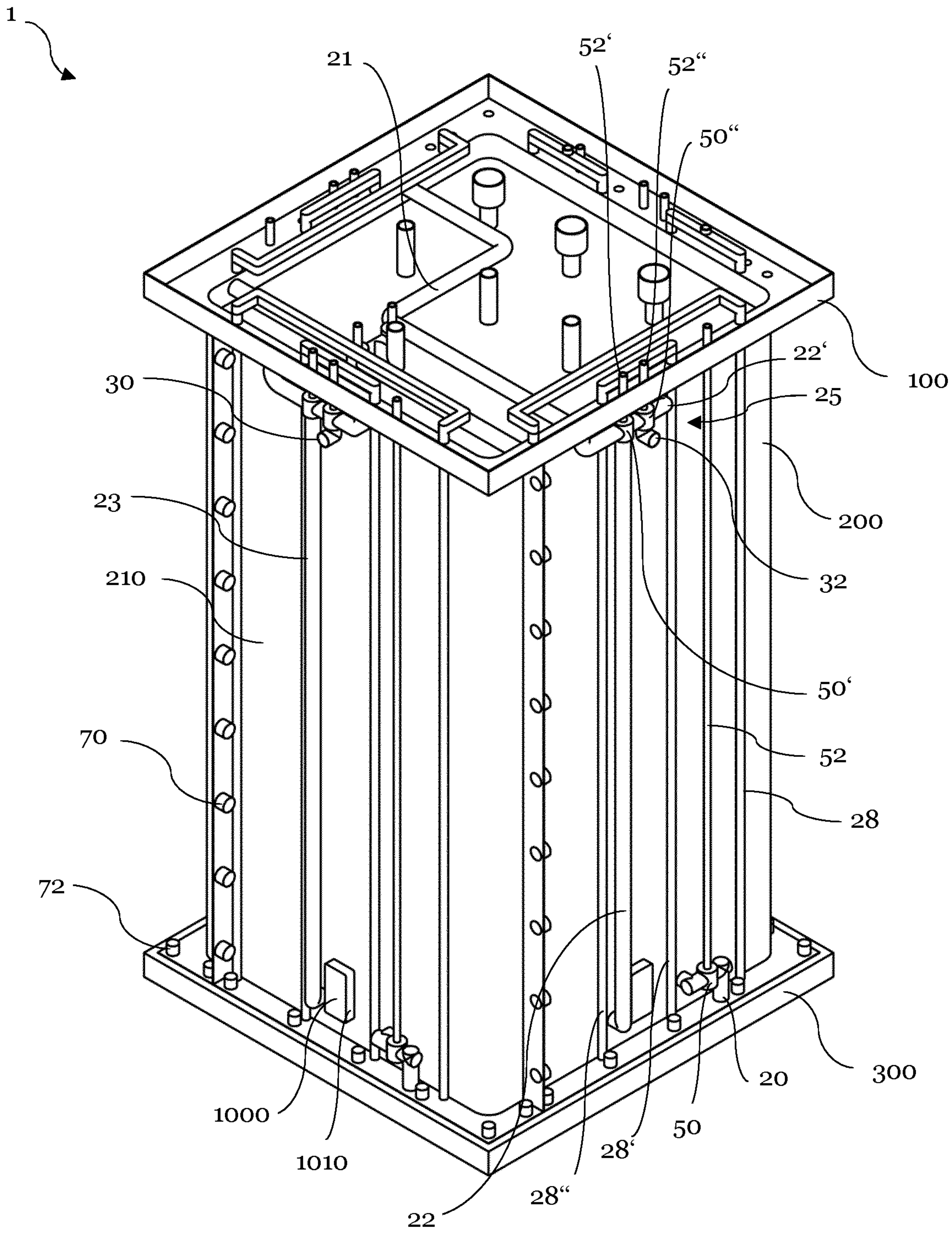
FIG. 2 schematically shows a smart tank in an assembled state.

FIG. 2 shows a smart tank 1 in an assembled state. This smart tank may serve for storing and/or transporting a biochemical medium. The shown smart tank comprises a top plate element 100, three sidewall elements 200, 210, and a bottom plate element 300. The top plate element, the sidewall elements and the bottom plate element are arranged to form a reservoir for receiving at least one biochemical medium.

The smart tank 1 comprises further channels 20, 21, 22, 23 for guiding the at least one biochemical medium and/or an operating medium. The channels extend within at least one of the top plate element 100, the sidewall elements 200, 210 and/or the bottom plate element 300. At least one of the channels extends within the top plate element 100 and at least one of the at least one sidewall element and/or the bottom plate element.

For example channel 21 extends in the sidewall element 200 and the top plate element 100. Other channels may be provided that extend in the at least one sidewall element and at least one of the top plate element and the bottom plate element. Each of the channels may be at least one of the following channel types: An inlet channel, for guiding a biochemical medium and/or an operating medium to the reservoir of the smart tank. An outlet channel, for removing a biochemical medium and/or an operating medium from the reservoir of the smart tank. A retentate channel, for transferring a retentate back into the smart tank or out of the smart tank. A bypass-channel, for guiding a biochemical medium and/or an operating medium, wherein the bypass-channel is not connected to the reservoir of the smart tank. Alternatively, the bypass-channel can be adapted to be fluidically separated from the reservoir of the smart tank, e.g. by means of a valve. A heating or cooling channel for guiding a tempered heating or cooling medium. A sampling channel, for taking a sample of biochemical medium and/or of operating medium from the reservoir of the smart tank. Particularly, the smart tank may comprise multiple channels of different channel-types and/or the same channel type.

In the smart tank shown in FIG. 2, channel 20 serves as outlet channel, particularly for removing waste. Channel 22 can be either an inlet or an outlet channel. This channel 22 enters the reservoir at a bottom side of the smart tank (i.e. near the bottom plate element). Channel 22' can also be either an inlet or an outlet channel. This channel 22 enters the reservoir at a top side of the smart tank (i.e. near the top plate element). Channel 21 is a bypass-channel, that allows guiding a biochemical medium and/or an operating medium, via the smart tank, without entering the reservoir of the smart tank. Channels 28, 28' and 28" are not connected to the reservoir and may serve as cooling and/or heating channels.

Channels 21, 22 and 22' meet each other at a channel junction 25. This channel junction is provided with at least one (in the embodiment shown with two) valves 50', 50". These valves 50', 50" are actuatable from the outside of the smart tank, by means of an actuating means 52', 52". The actuating means 52', 52" are provided in form of actuation rods. Channel 20 is associated with a respective valve 50 which can be actuated from the outside of the smart tank, by means of actuating means 52.

Further, the smart tank 1 comprises ports 30, 32. The ports are each associated with respective channel(s). The ports may be chosen from a group of port-types, comprising the following port-types: a fluid inlet port, a gas inlet port, a fluid outlet port, a gas outlet port, a cell bleed port, a medium supply port, a medium remove port, an element-interconnecting port, and a tank-interconnecting port.

For example, port 32 is associated via valves 52', 52" with channels 21, 22 and 22'. Accordingly, this port 32 may serve as fluid inlet port, gas inlet port, fluid outlet port, gas outlet port, medium supply port, medium remove port, or tank-interconnecting port. Chanel 20, which serves as outlet channel is associated with an outlet port (not shown) on a bottom side of the bottom plate element 300.

Particularly, all sides of the smart tank (or at least some of the sides) may provide the same port interface. I.e. ports are arranged at the same position. Thus, a smart tank can be easily interconnected to a further smart tank (cf. e.g. FIG. 9). Further, all side wall elements of a smart tank may be identically structured. Thus, the number of different elements required for setting up a smart tank is reduced.

Figure 3A:
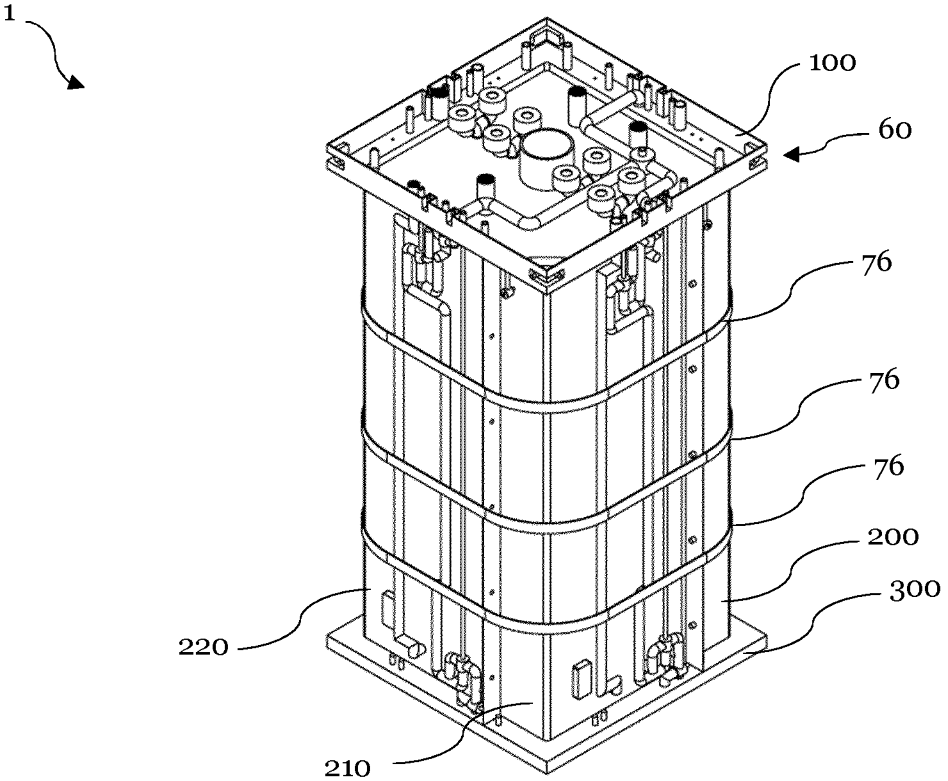
FIG. 3A schematically shows a smart tank comprising connector means.

FIG. 3A schematically shows a smart tank 1 comprising connector means 60, 62. The connector means 60, 62 are provided at a top plate element 100 of the smart tank 1. Alternatively, connector means may be provided at the top plate element 100, the at least one side wall element 200 and/or at the bottom plate element 300. The at least one connector means 60, 62 serves for interconnecting the smart tank 1 with a further smart tank 2 (cf. FIG. 3C). In a further configuration, the connector means may provide a fluidical connection and may further be adapted for interconnecting the smart tank fluidically with a further smart tank without using a hose. Particularly, the connector means may comprise a sealing member, that allows to seal the connection between to interconnected smart tanks. The sealing member may be integrally formed (e.g. using 2K-injection moulding) and/or may be assembled.

Figures 3B, 3C, 3D:
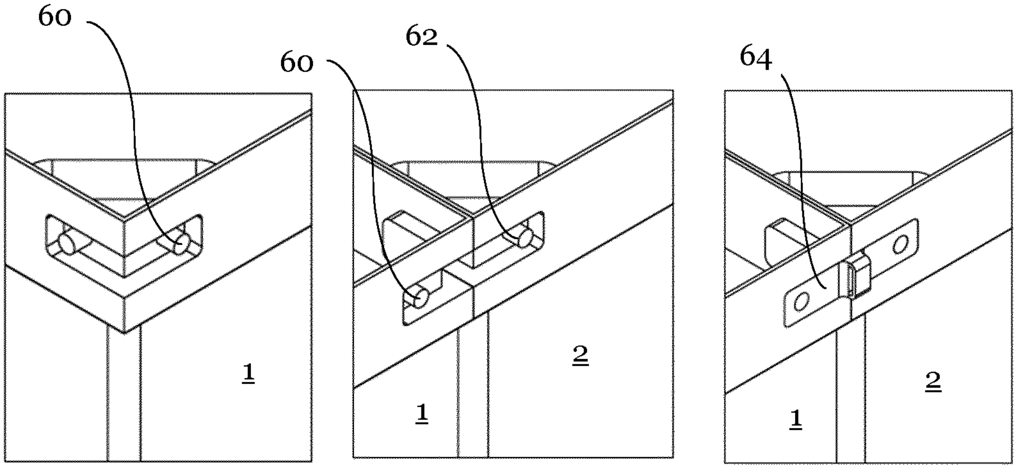
FIG. 3B gives a detailed view of the connector means.
FIG. 3C gives a detailed view of connector means of adjacent smart tanks.
FIG. 3D gives a detailed view of interconnected smart tanks.

The smart tank of FIG. 3A comprises a latching connector means 60 (cf. FIG. 3B), which is configured to latch with an inter-latching connector means 64 (cf. FIG. 3D). This inter-latching connector means 64 is adapted to latch with a latching connector means 62 of a further smart tank 2. Thereby smart tank 1 is directly interconnected with said further smart tank 2, via the inter-latching connector means 64.

The connector means 60, 62 may be a protruding connector means, as shown in FIG. 3B. Optionally, this protruding connector means is provided in a recess to be protected, e.g. during transport, from being damaged.

Figure 4:
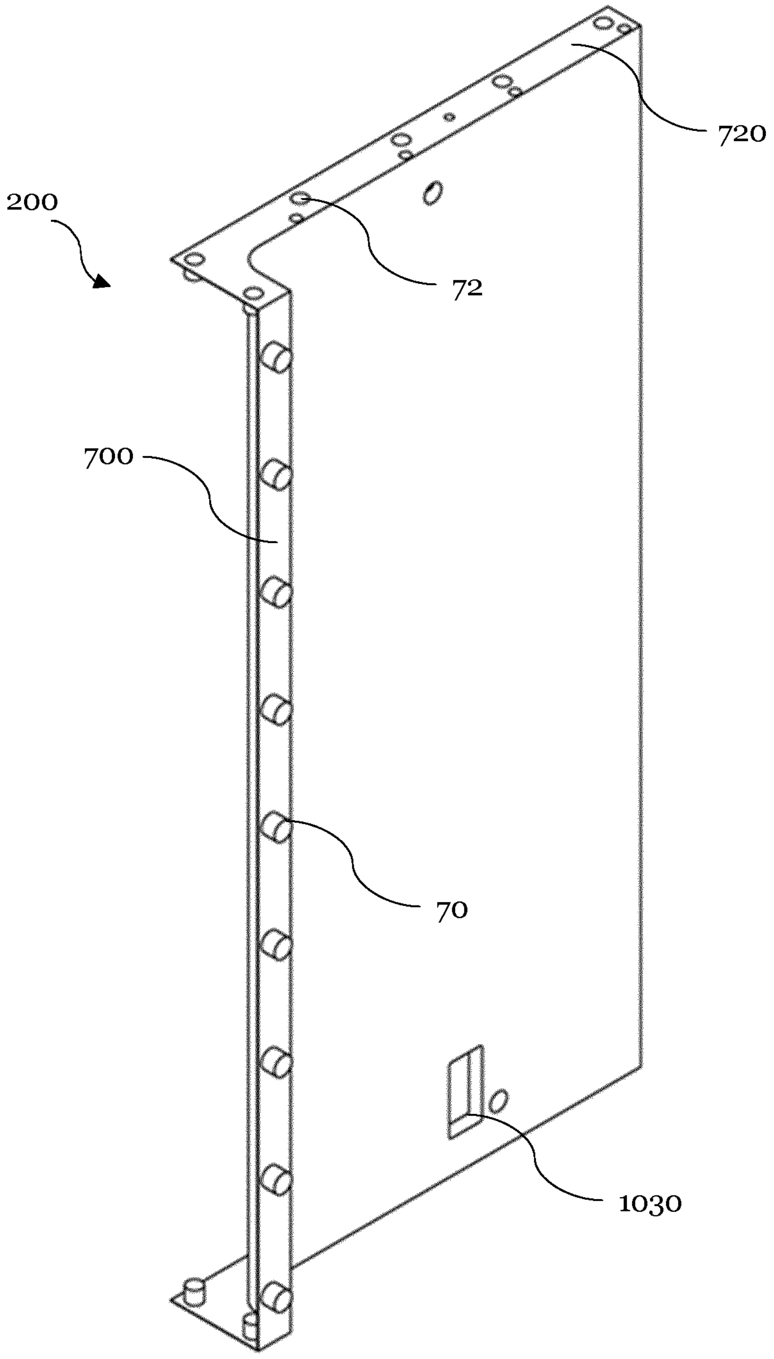
FIG. 4 schematically shows a sidewall element, having assembly-connecting means.

FIG. 4 schematically shows a sidewall element 200, having assembly-connecting means 70 and corresponding assembly-connecting means 72. The assembly-connecting means 70 are provided in form of protrusions that can engage with corresponding recesses, being provided on a further element, such as a further sidewall element, a top plate element and/or a bottom plate element. The corresponding assembly-connecting means 72 are provided in form of recesses that can engage with corresponding protrusions, being provided on a further element, such as a further sidewall element, a top plate element and/or a bottom plate element. The assembly-connecting means 70 and corresponding assembly-connecting means 72 are preferably equally distributed along the assembly connection faces 700, 720 that are in contact with corresponding assembly connection faces of a further element, when the smart tank is assembled.

Further, the sidewall element 200 may comprise at least one sealing member (not shown) for providing a sealed connection between the sidewall element and a further element, such as a top plate element 100, a further sidewall element 210, 220 and/or a bottom plate element 300. The sealing member may be arranged circumferentially at the sidewall element. When the elements are assembled to form the reservoir, the sealing member may be compressed, so as to provide a retaining force that acts on the assembly-connecting means 70 and/or the corresponding assembly-connecting means 72. Thereby, a self-retaining engagement can be provided.

As shown in FIG. 3A, the smart tank 1 may comprise assembly reinforcement means 76 for reinforcing the assembly of the top plate element 100, at least one of the sidewall elements 200, 210, 220 and/or the bottom plate element 300 of the smart tank. The assembly reinforcement means 76 may include a threaded means (not shown), such as a threaded rod, a strap 76 and/or a belt (not shown). The assembly reinforcement means 76 improve the tightness of the reservoir of the smart tank. Thus, leakage can be prevented.

Further, the sidewall element 200 may comprise a receptacle 1030, for receiving a sensor module 1000 or at least one sensor 1010. Particularly, the receptacle 1030, the sensor module 1000 and/or the at least one sensor 1010, may comprise a sealing member, that allows to seal the connection between sidewall element 200 and the sensor/sensor module. The sealing member may be integrally formed (e.g. using 2K-injection moulding) and/or may be assembled.

Figure 5:
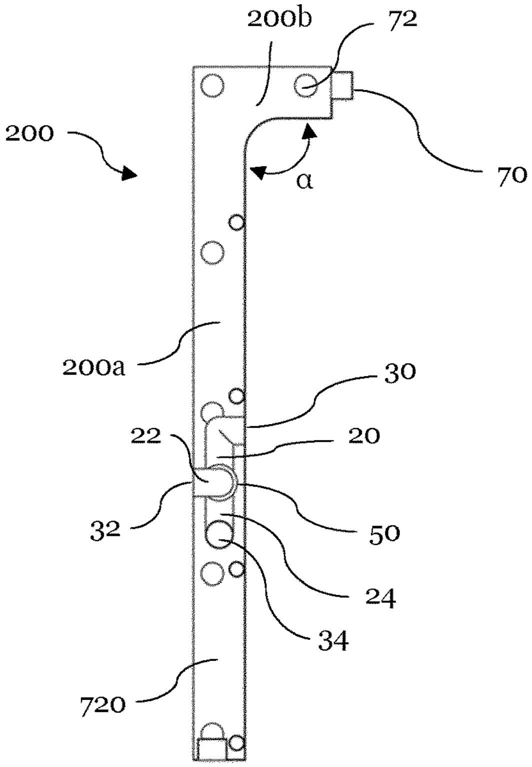
FIG. 5 schematically shows a sidewall element, comprising a channel.

FIG. 5 schematically shows a sidewall element 200, comprising channels 20, 22, 24. Those channels meet each other at a channel junction. This channel junction may be provided with a valve 50 for controlling the fluid flow. Channel 20 is associated with a port 30 that is provided on an inner surface of the sidewall element. Channel 22 is associated with a port 32 that is provided on an outer surface of the sidewall element. Channel 24 is associated with a port 34 that is provided on an assembly connection face 720. This port 34 serves as an element-interconnecting port (cf. also FIG. 6). The channels 20, 22, 24 form an inner lumen of the sidewall element that extends in the sidewall element and that is adapted to guide a flow of a biochemical medium and/or an operating medium. Particularly, the channels 20, 22, 24 are integrally formed with the sidewall element.

The sidewall element 200 of FIG. 5 comprises a first sidewall portion **200*a* and a second sidewall portion 200*b*. The first sidewall portion 200*a* and the second sidewall portion 200*b* enclose an angle α. Here, the angle α is about 90°. Thus, when assembled, the reservoir has a substantial rectangular cross-section, when seen from the top plate element side. Other angles, such as about 120° or about 135° are also possible. Accordingly, the assembled reservoir would then have a substantially hexagonal or octagonal cross-section, when seen from the top plate element side. As shown, the first sidewall portion 200*a* extends laterally farther than the second sidewall portion 200*b*. Thus, stability of the reservoir can be improved. Further, the inner edge formed by the first sidewall portion 200*a* and the second sidewall portion 200*b*** is provided in form of a rounded edge.

Figure 6:
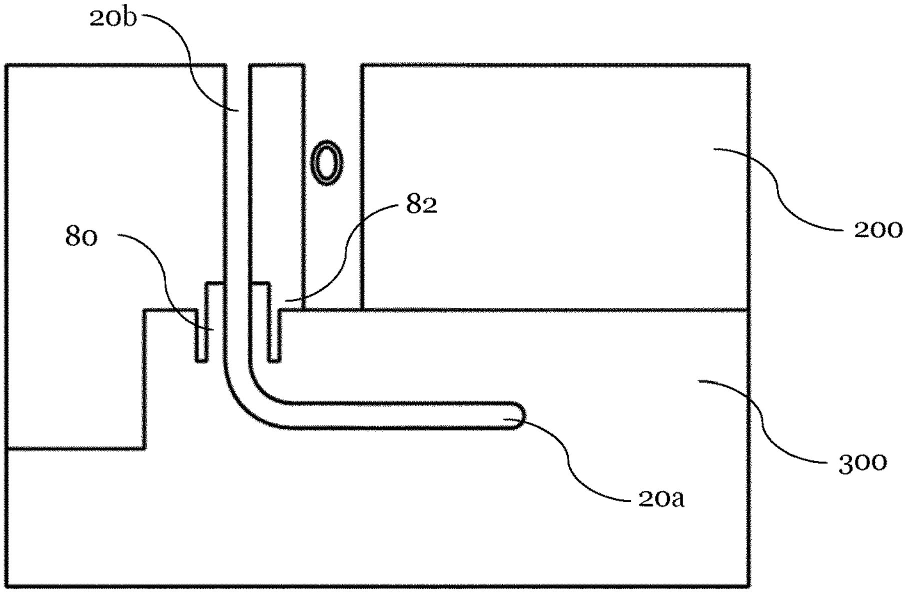
FIG. 6 schematically shows a channel-connecting means.

FIG. 6 schematically shows a bottom plate element 300 and an assembled side wall element 200. The sidewall element 200 comprises a first channel portion **20*b* and the bottom element a second channel portion 20***a*. The channel portions 20*a*, 20*b* are associated with a respective element-interconnecting port that includes a channel-connecting means. The channel-connecting means 82 is associated the first channel portion 20*b*. A corresponding channel-connecting means 80 is associated the second channel portion 20*a*.

The channel-connecting means 82 and the corresponding channel-connecting means 80 are configured to engage with each other, so as to form a fluidically sealed channel connection, between the first channel portion 20*b* and the second channel portion 20*a*. Both channel portions form a channel 20.

The corresponding channel-connecting means 80 comprises a protruding shroud that at least partially surrounds the end of the associated second channel portion 20*a*. The shroud is concentrically arranged around a channel end of the associated channel portion 20*a*. The channel-connecting means 82 comprises a recess, that at least partially surrounds the end of the associated channel portion 20*b*. The recess is concentrically arranged around the channel end of the associated second channel portion 20*b*. The channel-connecting means 82 and the corresponding channel-connecting means 80 may be formed to provide a positive locking. Particularly, the channel-connecting means 82 and the corresponding channel-connecting means 80 may include a quick-connector means. In the embodiment shown in FIG. 6, the sidewall element comprises a channel-connecting means 82. The bottom plate element comprises a corresponding channel-connecting means 80. This allows to couple the elements to form the reservoir of the smart tank and thereby to fluidically connect the respective channel portions 20*a*, 20*b* of the elements to form a connected channel 20, when assembling the smart tank. Thus, a medium can be guided though the channel 20 formed in at least two elements of the smart tank.

The channel-connecting means 82 and/or the corresponding channel-connecting means 80 may include a sealing member (not shown). Said sealing member may be a radial and/or an axial sealing member. For example, the sealing member may be provided on a shroud and/or within a recess of the channel-connecting means/corresponding channel-connecting means.

The element (top plate element, sidewall element and/or bottom plate element) may comprise multiple channel-connecting means and/or the corresponding channel-connecting means to provide a channel-connecting interface that allows to easily assemble the smart tank. The channel-connecting interface may be configured to allow assembly of different elements. For example, a sidewall element may be assembled with a top plate element or a further sidewall element, using the same channel-connecting interface.

The channel-connecting means and the respective channel portions may be arranged to built a channel, that is adapted to guide a medium multiple times through an element (e.g. a side wall element) of the smart tank. This channel may be used as a heating or cooling channel and is configured to provide a uniformly tempered surface of the respective element.

Figure 7:
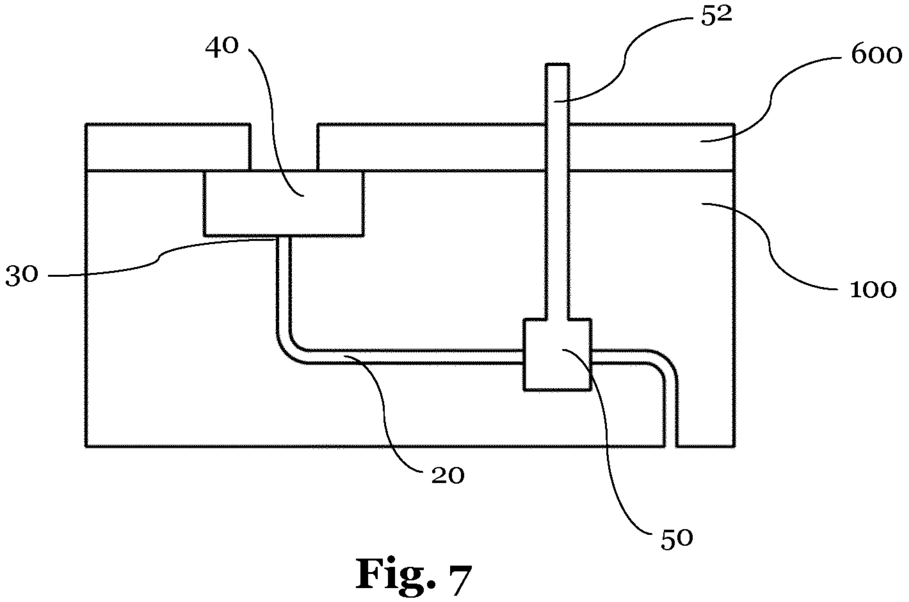
FIG. 7 schematically shows a top plate element, comprising a valve.

FIG. 7 schematically shows a top plate element 100 that comprises a valve 50 for opening/closing channel 20. The valve 50 is a mechanical valve that is configured to be actuatable from the outside of the smart tank, by means of an actuating means 52. The actuating means 52 is provided in form of an actuation rod that can be actuated from the outside of the smart tank, e.g. by a handling manipulator. For opening/closing the channel, the actuating means 52 can be rotated or axially displaced, depending on the type of associated valve. The actuating means may be supported in an adaptor plate element 600 that can be installed on top of the top plate. The adaptor plate element may cover a filter 40 and/or a port 30 at least partially. Thus, operating and/or biochemical medium can be guided to the smart tank via the filter 40.

Generally, all channels and/or reservoirs of the smart tank may be configured to be self-emptying. I.e. medium that has entered the channel and/or reservoir can flow out of the respective channel and/or reservoir by gravitation.

Figure 8:
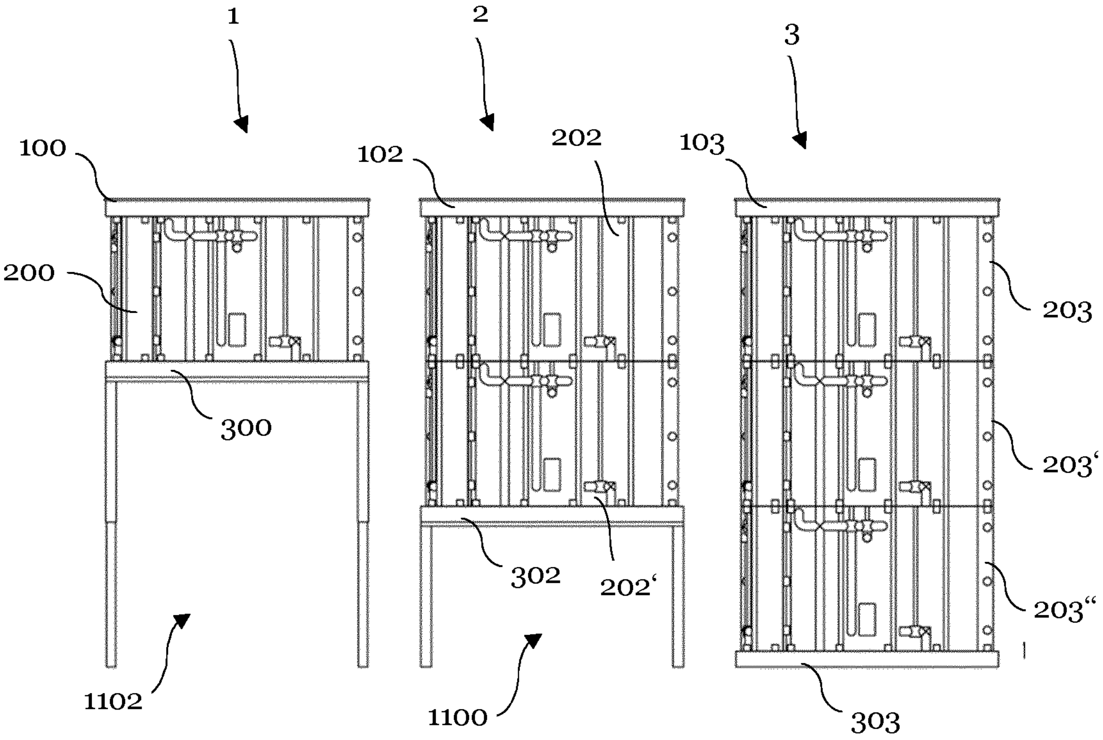
FIG. 8 schematically shows smart tanks, having different volumes.

FIG. 8 schematically shows smart tanks 1, 2, 3, having different volumes. To provide different volumes, it is possible to provide different kinds of sidewall elements. Thus, different volumes can be provided, using the same top plate element and bottom plate elements.

Further, different volumes can be provided by stacking multiple sidewall elements 202, 202'; 203, 203', 203". As shown in FIG. 8, smart tank 1 comprises sidewall elements 200 that are all arranged in the same level of the smart tank 1. This smart tank has the following stack of elements: bottom plate element 300/side wall element 200/top plate element 100.

Smart tanks 2 and 3 comprises multiple sidewall elements 202, 202'; 203, 203', 203", wherein the groups of side wall elements are arranged in different levels of the smart tank. Smart tank 2 has the following element stack: bottom plate element 302/side wall element 202'/sidewall element 202/top plate element 102 and smart tank 3 has the following element stack: bottom plate element 303/side wall element 203"/side wall element 203'/sidewall element 203/top plate element 103.

As described above, channel portions extending in the respective sidewall elements are interconnected with corresponding channel portions in the neighboring element (sidewall element, bottom plate element or top plate element). Likewise, actuating means for actuating a valve and/or for driving a stirring means and/or the like that are provided in the sidewall element(s) may be coupled to corresponding actuating means of a neighboring element. Thus, a valve or the like provided e.g. in sidewall element 202' or 203" can be actuated from the top side of the smart tank.

As shown, the height dimension of the first smart tank 1 is smaller than a height dimension of the second smart tank 2 and the third smart tank 3. To provide the top plate elements 100, 102 and 103 on substantially the same height, a height compensation means 1100, 1102 can be provided. For example, the height compensation means may comprise a telescope mechanism or a folding mechanism for adjusting the height of the height compensation means. Said height compensation means 1100, 1102 is adapted to be coupled to the smart tank 1, 2 and allows to install the top plate element 100 of the first smart tank 1, the top plate element 102 of the second smart tank 2 and in substantially the same height as the top plate element 103 of the third smart tank 3. Thus, interconnection of the smart tanks is facilitated.

Figure 9A:
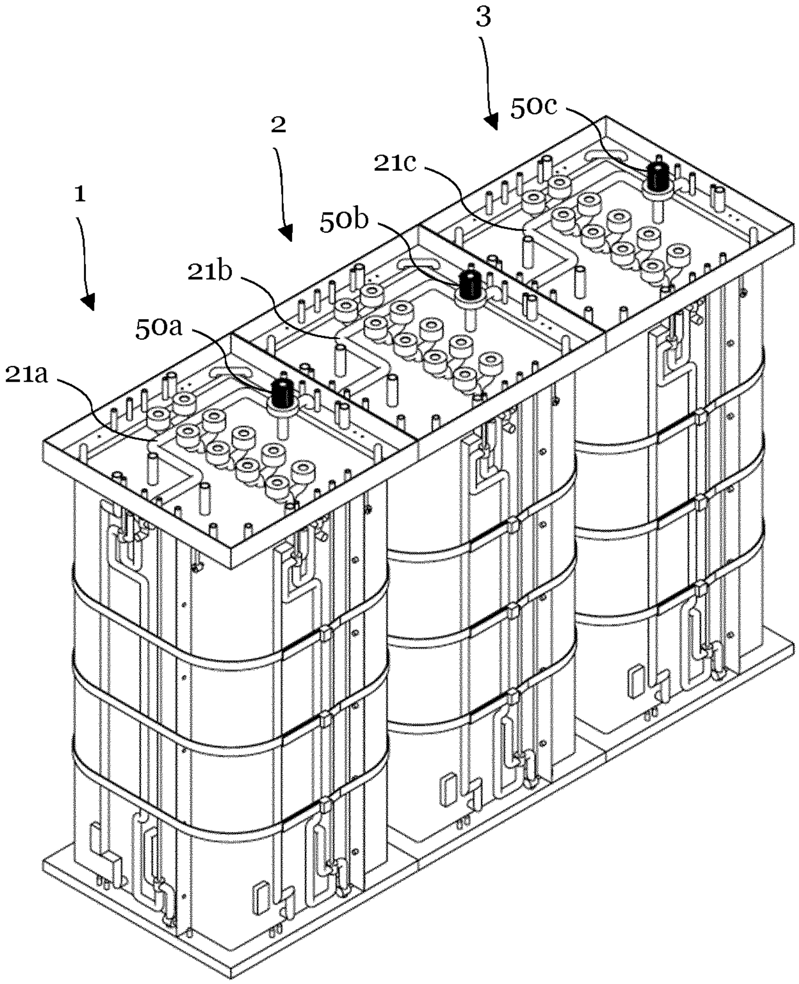
FIG. 9A schematically shows a smart tank system.

FIG. 9A schematically shows a smart tank system that comprises multiple smart tanks 1, 2, 3. The smart tanks are directly interconnected with each other. At least one of the one or more channels 21*a* of the first smart tank 1 is fluidically connected to a respective channel 21*b* of the second smart tank 2 which can be connected to a respective channel 21*c* of the third smart tank. Depending on the position of the valves 50*a*, 50*b* and/or Soc. Medium can be e.g. transferred from the first smart tank to the second smart tank or the third smart tank. When transferring medium to the third smart tank medium can either be guided through the reservoir of the second smart tank or medium can bypass the reservoir of the second smart tank.

Figure 9B:
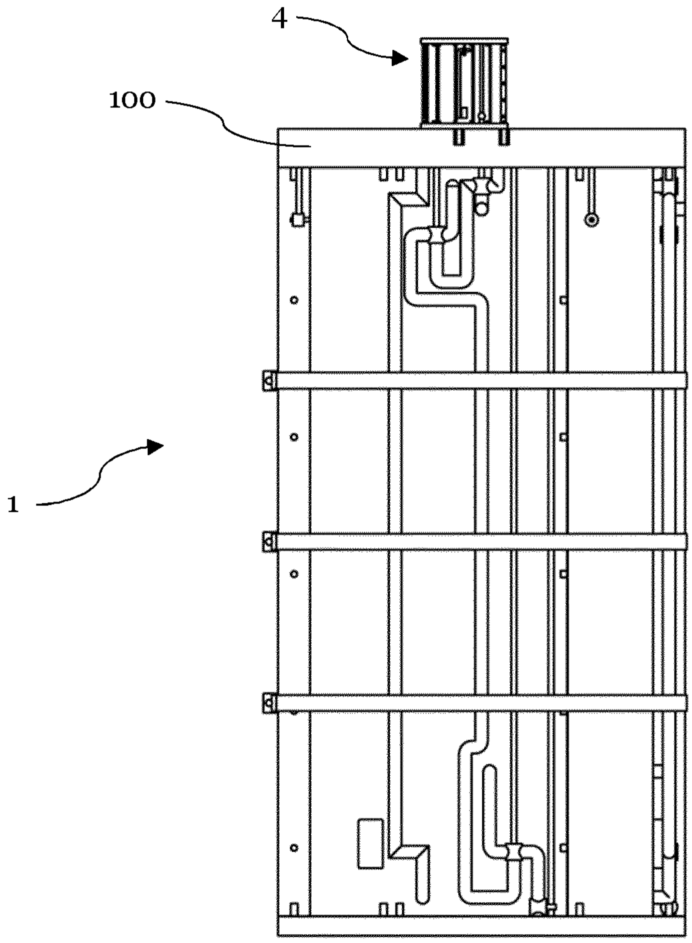
FIG. 9B schematically shows a further smart tank system.

FIG. 9B schematically shows a further smart tank system. The smart tank system comprises two smart tanks, a larger smart tank 1 and a smaller small tank 4. The smaller smart tank 4 is provided on top of the larger smart tank 1. The smaller smart tank 4 can be provided on top of the larger smart tank 1 by using the handling manipulator (not shown). The handling manipulator may comprise a gripping device that is adapted to grip the smaller smart tank and to put it on top of the larger smart tank 1. Both smart tanks may be fluidically connected, via a channel or port (not shown). The channel or port may comprise a sterile filter, allowing to transfer medium from the smaller smart tank to the larger smart tank without contaminating the larger smart tank. The fluid connection may be controlled by a valve that is preferably operable by at least one handling manipulator. The smaller smart tank may serve to provide an operating medium and/or a biochemical medium to the larger smart tank. As the smaller smart tank 4 is installed on top of the larger smart tank 1, it is possible to transfer medium from the smaller smart tank to the larger smart tank by using gravitation. Alternatively, medium can be transferred by providing a positive pressure to the smaller smart tank and/or by providing a negative pressure to the larger smart tank. Further, the smaller smart tank may be provided outside the clean room bag, wherein the larger smart tank may be provided within the clean room bag.

Figure 10:
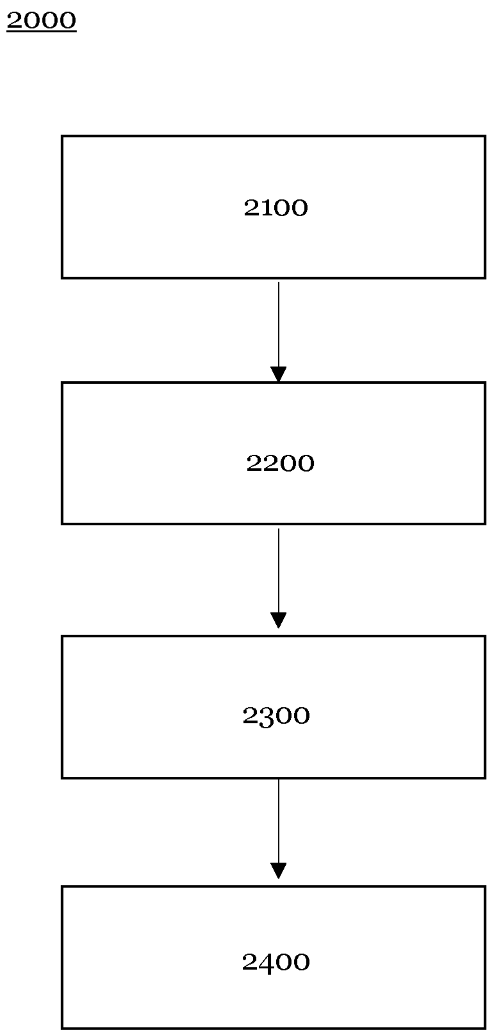
FIG. 10 schematically shows a flow diagram of a method for assembling a smart tank.

FIG. 10 schematically shows a flow diagram of a method 2000 for assembling a smart tank. The method comprises the following steps: providing 2100 a top plate element; providing 2200 at least one sidewall element; providing 2300 a bottom plate element and assembling 2400 the top plate element, at least one sidewall element, and a bottom plate element to form a reservoir for receiving at least one biochemical medium.

Figure 11:
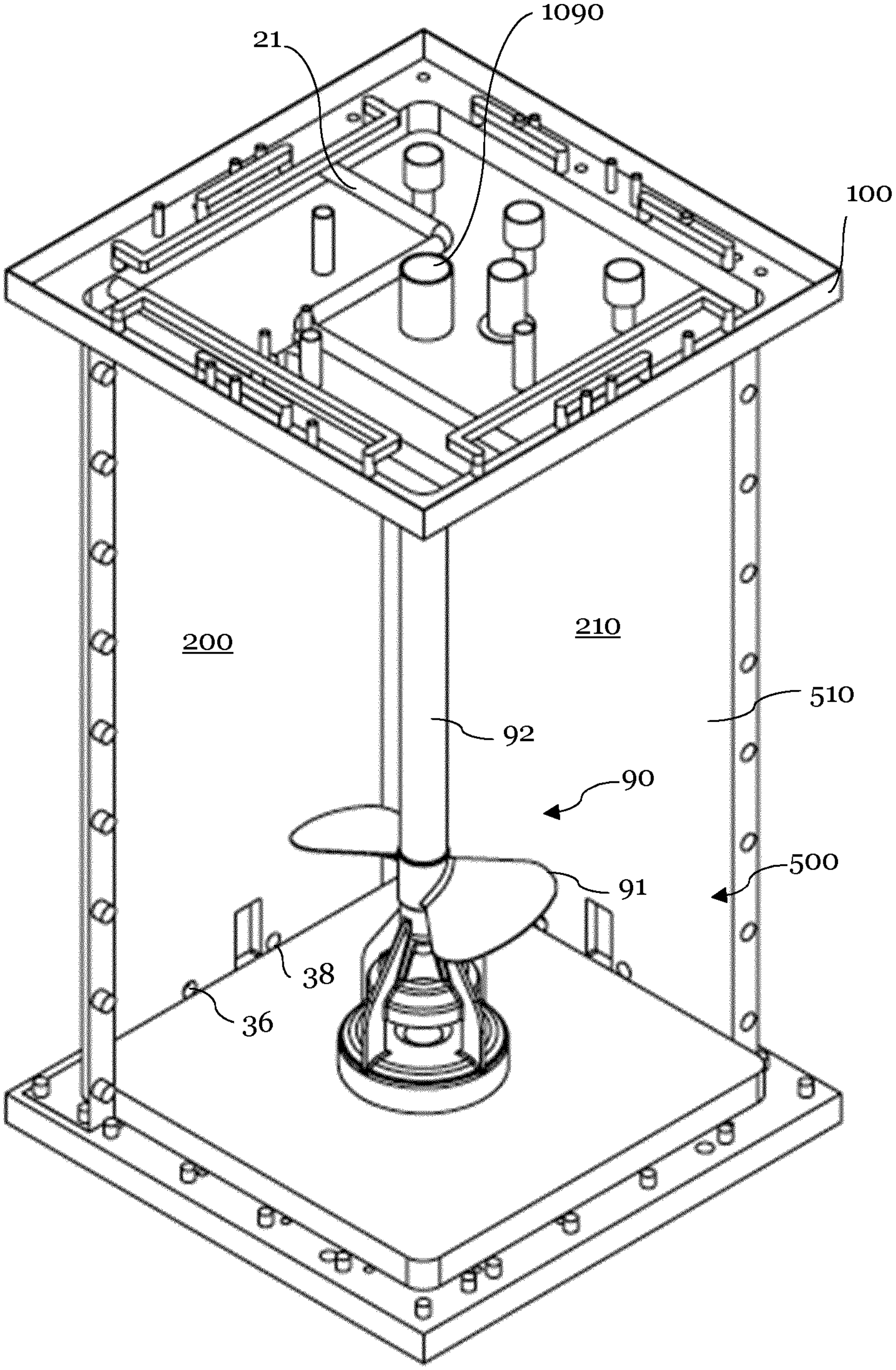
FIG. 11 schematically shows a smart tank.

FIG. 11 schematically shows a smart tank. This smart tank may serve for transporting and storing a biochemical medium. The smart tank comprises a stirring means 90. The smart tank shown in FIG. 11 corresponds to the smart tank described with respect to FIG. 2, wherein two sidewall elements are removed. To allow a view inside the reservoir 500 of the smart tank. The inner surface 510 of the reservoir may be coated e.g. by a glass coating.

The stirring means 90 comprises at least one stirring member 91, wherein the stirring member comprises multiple stirring blades. Further, the stirring means comprises an actuating rod 92. Said actuating rod 92 is supported and sealed in the top plate element 100 of the smart tank. The actuating rod is engageable with a drive mechanism (not shown), such as an electric drive mechanism, provided on the outside of the smart tank. The drive mechanism may be part of a handling manipulator (not shown) that allows automated control of the smart tank and/or a smart tank system.

Further, in the lower portion of sidewall element 200, two outlet ports 36, 38 are shown that are associated with channels 20, 22, respectively (cf. FIG. 2). Ports 36, 38 may also serve as inlet ports.

Figure 12:
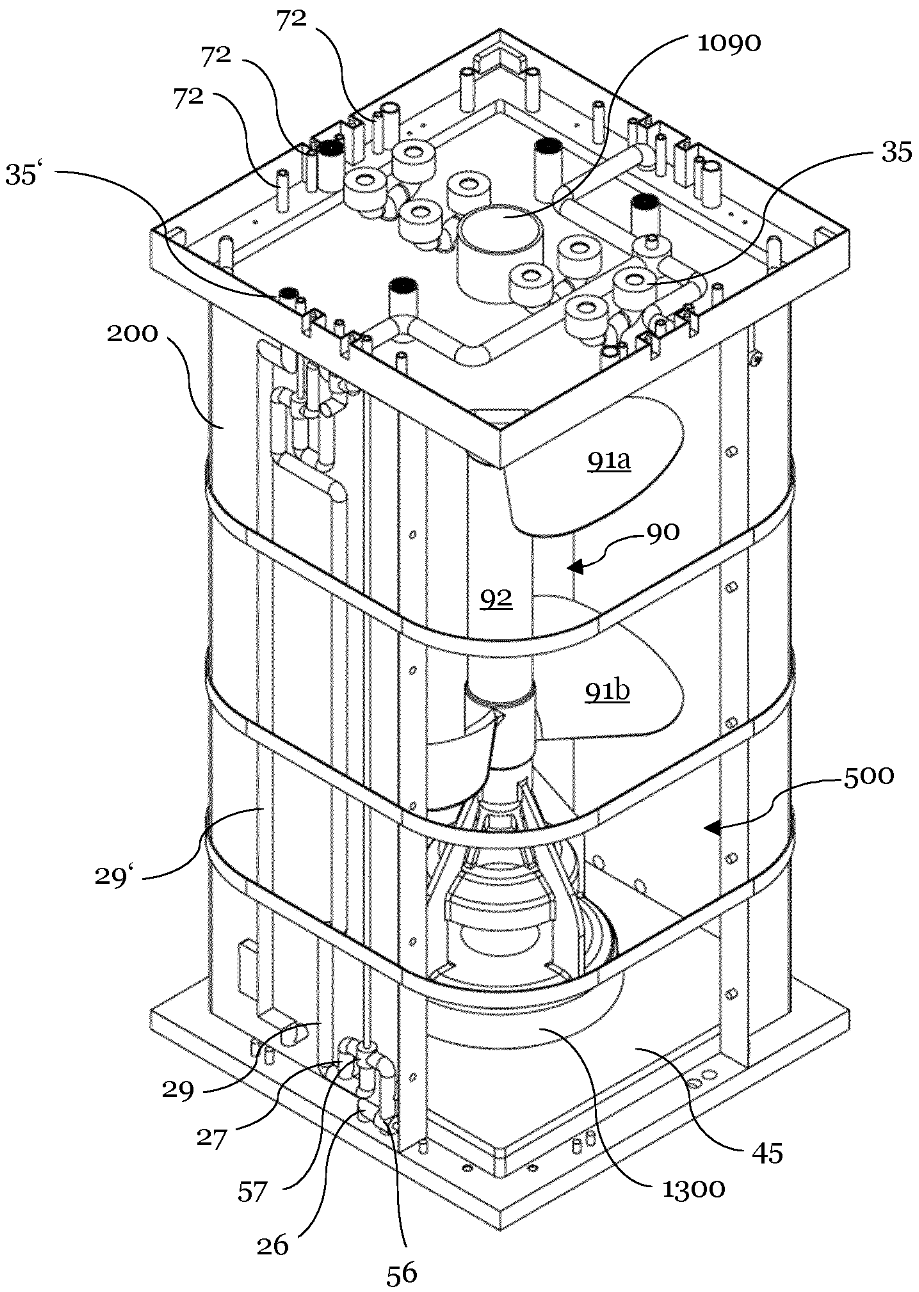
FIG. 12 schematically shows a further smart tank.

FIG. 12 schematically shows a further smart tank. Said smart tank may serve as a bioreactor, e.g. for growing and/or cultivating cells. This smart tank comprises a filter 45, provided with in the reservoir 500. The filter separates the reservoir 500 in two parts, a permeate side below the filter and a retentate side, above the filter.

The filter 45 may be a membrane filter that is supported by at least one rigid support structure, such as a support grating or mesh. The membrane may be a plastic membrane, preferably with homogeneous pores (i.e. not funnel-shaped). Thus, when cultivating cells, the cells do not penetrate the membrane but are retained on the surface. The membrane may comprise at least one of the following materials: PC, PET, PES, PVDF, CA, RC, or the like. The pore size of the membrane may be in a range of about 0.8 μm to 2 μm, preferably in a range of about 0.8 μm to 1.2 μm. This pore size allows to retain cells. The solvent of the cell solution can be collected on a permeate side of the filter and transferred back to the reservoir. Thus, it can be reused.

Moreover, the pore size may be in a range of about 0.1 μm to 0.8 μm. This pore size allows to retain *Mycoplasma* and/or viruses.

Further, the pore size may be in a range of about 100 μm to 300 μm. This pore size allows to retain micro carriers. Depending on the application, different pore sizes may be used. Further, the pore size may be smaller than 0.1 μm.

For removing retentate (e.g. cells) out of the smart tank, an outlet channel 27 is provided in the sidewall element 200, that is in fluidic communication with the retentate side. Said outlet channel may be associated with a cell bleed port. Via the cell bleed port, cells may be transferred to a further smart tank, e.g. a bio reactor smart tank, and/or the cells may be discarded.

Further, for removing permeate/filtrate out of the smart tank, an outlet channel 26 is provided in the sidewall element 200, that is in fluidic communication with the permeate/filtrate side. The outlet channel 26 may be opened to an outlet port (not shown), via valve 56. A further channel 29 is provided that meets the outlet channel 26 and the outlet channel 27 at a channel junction. A valve 57 is associated with said channel junction. Depending on the position of valves 56, 57 permeate and/or retentate can be guided to the outlet port, or to channel 29 for e.g. being transferred to a further smart tank. Likewise, filtrate and/or retained medium can be guided to the outlet port, or to channel 29 for e.g. being transferred to a further smart tank. Further, a channel 29' may serve to guide an operating medium, such as pressured air directly to the permeate side/filtrate side. Thus, the filter can be flushed and retentate can be transferred back into the reservoir (retentate side, upstream side) and/or permeate can be urged from a permeate side of the filter back into the reservoir and/or to a further smart tank. Respectively, filtrate can be urged from a filtrate side of the filter back into the reservoir and/or to a further smart tank.

The smart tank of FIG. 12 also comprises a stirring means 90, having two stirring members 91*a*, 91*b*. As described with respect to FIG. 11, the stirring means 90 comprises an actuating rod 92, wherein the stirring means 90 can be actuated via the actuating rod 92. In particular, the stirring means 90 may be operated in a pulsed mode. Thereby waves are created that allow to clean up the filter 45 from the retentate side. Further, for controlling the filtering, pressurized air can be provided to the retentate side, e.g. by gas inlet port 35'. The gas inlet port may be covered by a filter, such as a sterile filter to provide sterile pressurized air to the smart tank. Port 35 may serve to provide further biochemical and/or operating medium to the reservoir of the smart tank. Each port may be associated with a respective filter.

Further, biochemical medium (gaseous and/or fluidic) may be supplied to the reservoir of the smart tank by means of a sparger 1300. The sparger may be provided as ring sparger.

Figure 13:
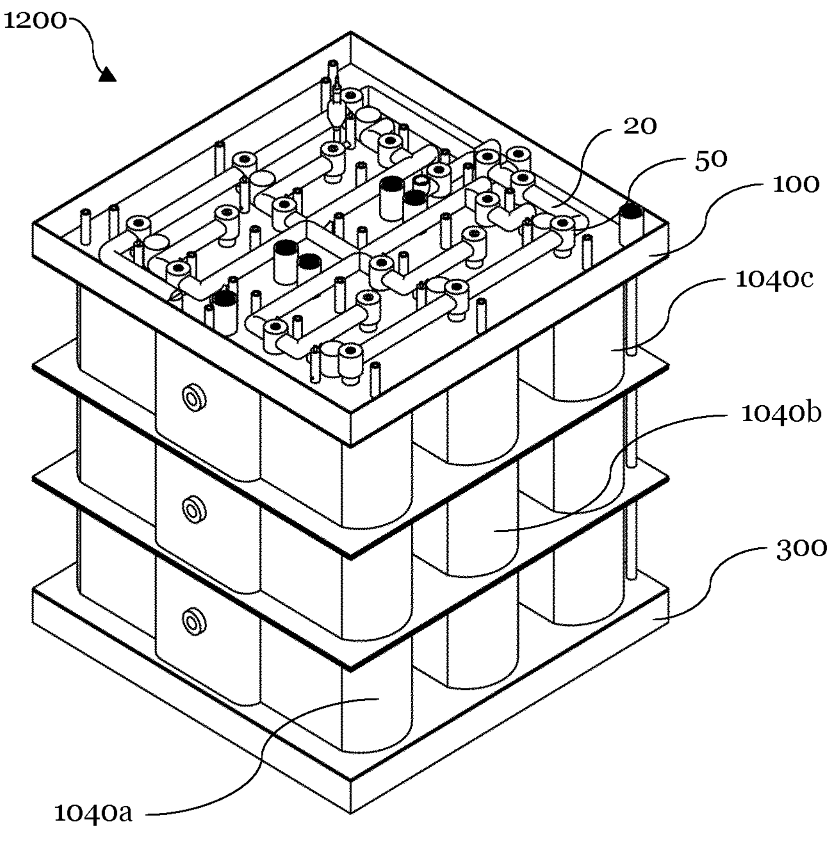
FIG. 13 schematically shows a further smart tank.

FIG. 13 schematically shows an even further smart, comprising filter cartridges 1040*a*, 1040*b*, 1040*c*. This smart tank may be used for sterile filtering. The first filter cartridge 1040*a* may comprise a prefilter and the following filter cartridges 1040*b*, 1040*c* respective sterile filters. The filter cartridges are sidewall elements and each of the filter cartridges forms with the top plate element 100 and the bottom plate element 300 a respective reservoir. The filter cartridges 1040*a*, 1040*b*, 1040 can be connected via a channel network 1200, comprising multiple channels 20 and valves 50. The channels and valves are arranged so that medium can be transferred to the filter cartridges 1040*a*, 1040*b*, 1040*c* serially or parallelly. In particular, by choosing respective positions of the valves of the channel network 1200 the flow of the medium can be guided through the filter cartridges as required. For example, medium can be fed back to filter cartridges 1400*a* after having serially passed all three filter cartridges 1040*a*, 1040*b*, 1040*c*. Further, the channel network 1200 and corresponding valves allow to provide integrity testing of each of the filter cartridges. In case of serially arranged filters, the pore size of the filters may decrease. Thus, a coarse filter is followed by finer filters.

Figure 14:
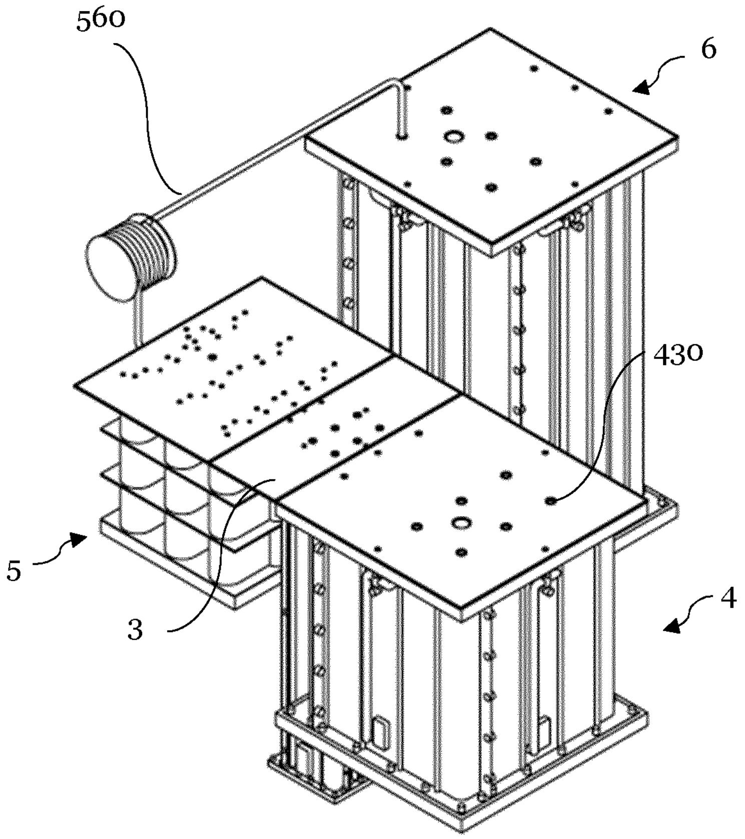
FIG. 14 schematically shows a smart tank system including the smart tank of FIG. 13.

FIG. 14 schematically shows a smart tank system comprising the smart tank described with respect to FIG. 13. This smart tank system may serve for preparing buffer solutions and/or media. In a first smart tank 4, a medium, such as water for injection may be provided. Via at least one inlet port 430, that is associated with a respective valve (not shown) buffer medium can be provided to said first smart tank 4 in a controlled manner. Preferably, at least one capsule (not shown) comprising said buffer medium is installed directly on top of the top plate element of the first smart tank. The buffer medium may be provided in liquid or solid form (e.g. in form of a powder, crystals, granulate, and/or the like). For transferring a solid medium to smart tank 4, a vibrating means may be provided (e.g. at a handling manipulator) that allows to control a dose of solid medium supplied to the smart tank.

The medium and the buffer medium can be mixed in the first smart tank 4 and subsequently guided to the second smart tank 3, that servers further mixing. From the second smart tank 3, the medium and the buffer medium can be transferred to a third smart tank 5. The third smart tank 5 may be the smart tank described with respect to FIG. 13. The filtered medium can then be guided to a fourth smart tank 6, which may be a bioreactor. The transfer of the medium can be achieved by a hose means 560. This configuration allows to prepare further buffer solution and/or media in the first smart tank, while previously prepared buffer solution and/or media is mixed in the second smart tank.

Figure 15:
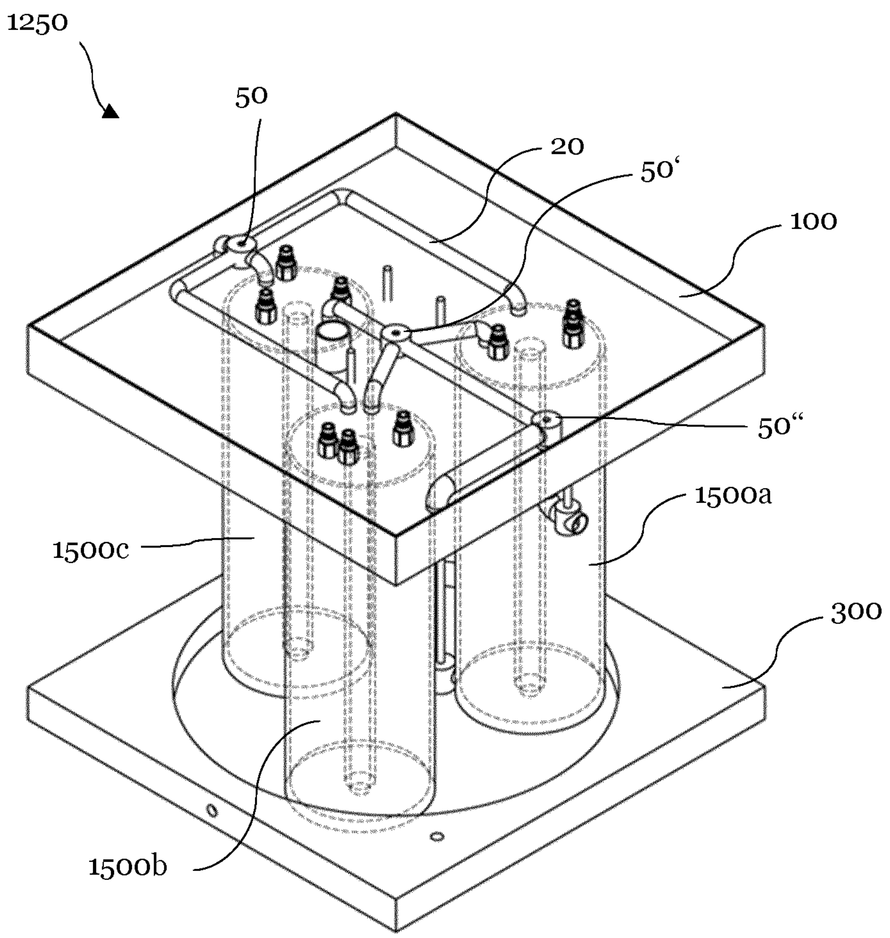
FIG. 15 schematically shows a further smart tank.

FIG. 15 schematically shows an even further smart tank, comprising cartridges for chromatography 1500*a*, 1500*b*, 1500*c*. This smart tank serves for chromatography. The cartridges for chromatography 1500*a*, 1500*b*, 1500*c* are sidewall elements and each of the cartridges for chromatography 1500*a*, 1500*b*, 1500*c* forms with the top plate element 100 and the bottom plate element 300 a respective reservoir. The cartridges for chromatography 1500*a*, 1500*b*, 1500*c* are connected via a channel network 1250, comprising multiple channels 20 and valves 50, 50', 50". The channels and valves are arranged so that medium can be transferred to the chromatography 1500*a*, 1500*b*, 1500*c* serially or parallelly. In particular, the valves may be controlled, that the first cartridge 1500*a* and the second cartridge 1500*b* are arranged serially. Thus, medium expelling from the first cartridge 1500*a* is guided to the second cartridge 1500*b*, without spilling any medium. While the first and second cartridges 1500*a*, 1500*b* are in loaded, the third cartridge 1500*c* can be eluted, washed and cleaned. After the first cartridge 1500*a* is filled, the second and third cartridges 1500*b*, 1500*c* can be connected in series, by opening/closing the valves respectively and the first cartridge 1500*a* can be eluted and cleaned. This can be repeated, so that a continuous chromatography is possible. Thus, chromatography can be carried out continuously.

A smart tank may use multiple cartridges for chromatography, such as at least three cartridges for chromatography, preferably at least seven cartridges for chromatography or even more preferably at least 9 cartridges for chromatography.

For loading different solutions to the cartridges for chromatography, i.e. for washing, cleaning, eluding, a magazine may be provided that carries different reservoirs for each of said solutions. Each reservoir may have a respective outlet port that is arranged so that it can be connected to an inlet port, associated with a cartridge for chromatography. The inlet ports and/or outlet ports may be arranged relative to each other, that the reservoirs of the magazine may be coupled to any of the cartridges for chromatography by rotating the magazine.

Instead of a magazine that carries different reservoirs for each of said solutions, respective solution supply lines may be provided Each of the solution supply lines may have a respective outlet port that is arranged so that it can be connected to an inlet port, associated with a cartridge for chromatography. The solution supply lines and in particular the respective outlet ports may be arranged on a first body and the inlet ports may be arranged on a second body. First and second body may be rotatable with respect to each other, preferably by using a handling manipulator. Particularly, first and second body may be rotatable with respect to each other, so that each of the solution supply lines may be coupled to any of the cartridges for chromatography. Each of the solution supply lines may be coupled to a respective solution containing tank. Preferably, the second body is fixed relative to the smart tank and the first body is arranged rotatable with respect to the second body, or vice versa.

Still further, a rotatable intermediate body may be provided that is arranged between the first and second body. The intermediate body may comprise intermediate channels that are suited to fluidically couple any one of the outlet ports with any one of the inlet ports. Upon rotation of the intermediate body, each of the solution supply lines may be coupled to any of the cartridges for chromatography.

Alternatively, an intermediate rotatory coupling element may be provided that comprises channels that connect the inlet ports of the cartridges for chromatography with respective outlets of the reservoirs. By rotating a valve portion of the intermediate rotatory coupling element, the connections of the inlet ports with the outlet ports can be changed simultaneously, so that the reservoirs of the magazine may be coupled to any of the cartridges for chromatography by rotating the valve portion.

Figure 16A:
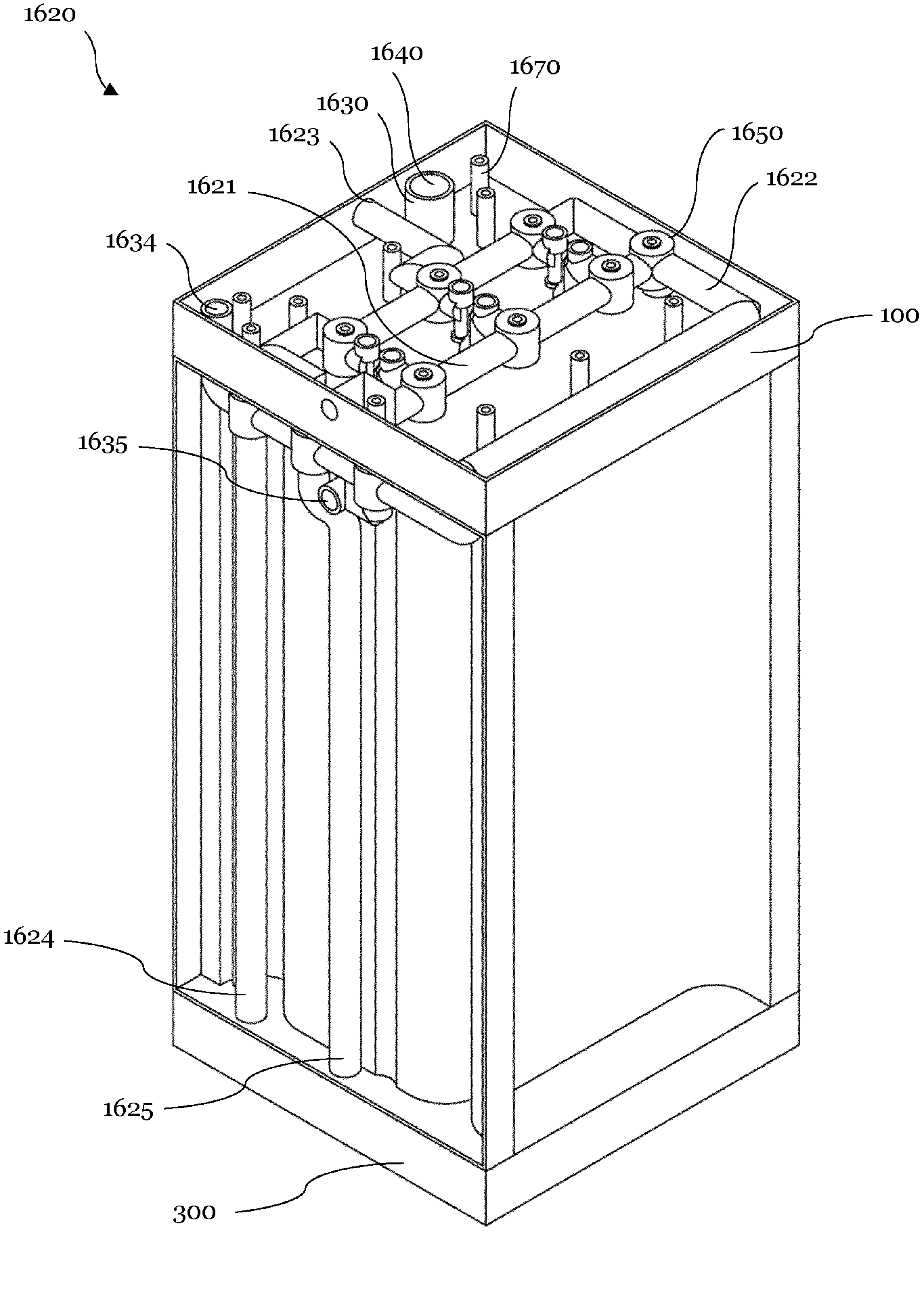
FIG. 16A schematically shows a perspective top view shows a further smart tank.
Figure 16B:
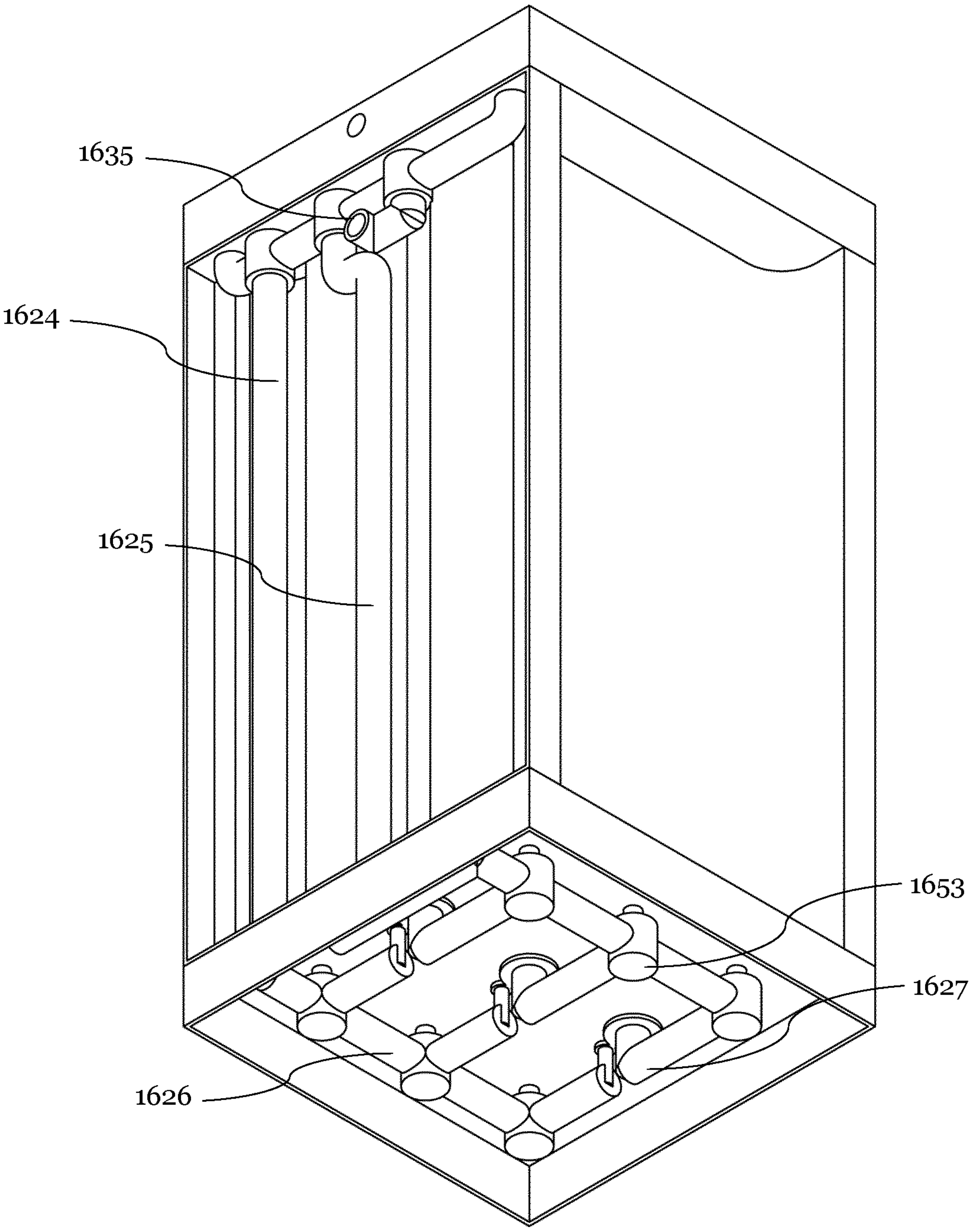
FIG. 16B schematically shows a perspective bottom view of the smart tank of FIG. 16A.

FIG. 16A schematically shows a further smart tank in a perspective top view and FIG. 16B shows a perspective bottom view of the smart tank. The smart tank comprises filter cartridges, such as a hollow fibre filter means (not shown). In particular, the smart tank comprises a channel network 1620, comprising multiple channels and valves 1650, 1653. The valves may be provided in the top plate element 100 and/or the bottom plate element 300. Valves 1650 can be operated from outside the smart tank on the top plate element side. For operating valves 1653, which are provided in the bottom plate element 300, multiple actuating rods 1670 are provided. Each actuating rod 1670 is associated with a respective valve 1653. Thus, valves 1653 can be operated from outside the smart tank on the top plate element side. The channels and valves are arranged so that medium can be transferred to the filter cartridges serially or parallelly. In particular, by choosing respective positions of the valves of the channel network 1620 the flow of the medium can be guided through the filter cartridges as required. Further, the channel network and corresponding valves allow to provide integrity testing of each of the filter cartridges.

In particular, the channel network comprises a permeate channels 1621, 1624, 1626 that is adapted to guide medium from a permeate side of the filter cartridges (i.e. from the bottom of the smart tank) to a waste channel 1623, an output port 1635 for transferring the permeate to e.g. a further smart tank, or to a recirculation channel 1622, that allows to feed back the permeate to at least one of the filter cartridges, e.g. via input channel 1625, 1627. Further, retentate may be recirculated. How the medium is guided is dependent on the position of the valves 1650, 1653. Further, for wetting the filters of the filter cartridges, e.g. prior to integrity testing, a wetting medium input port 1634 may be provided. Further, for applying operating medium, such as pressurized air to the permeate side of the filter cartridges, a operating medium input port 1630 may be provided. This operating medium input port 1630 may be covered by an air filter 1640, preferably a sterile air filter, that allows to provide sterile pressurized air to the permeate side of the filter cartridges. In other words, in the smart tank shown, pressurized air can be guided to the permeate channels of the bottom plate element.

Figure 17:
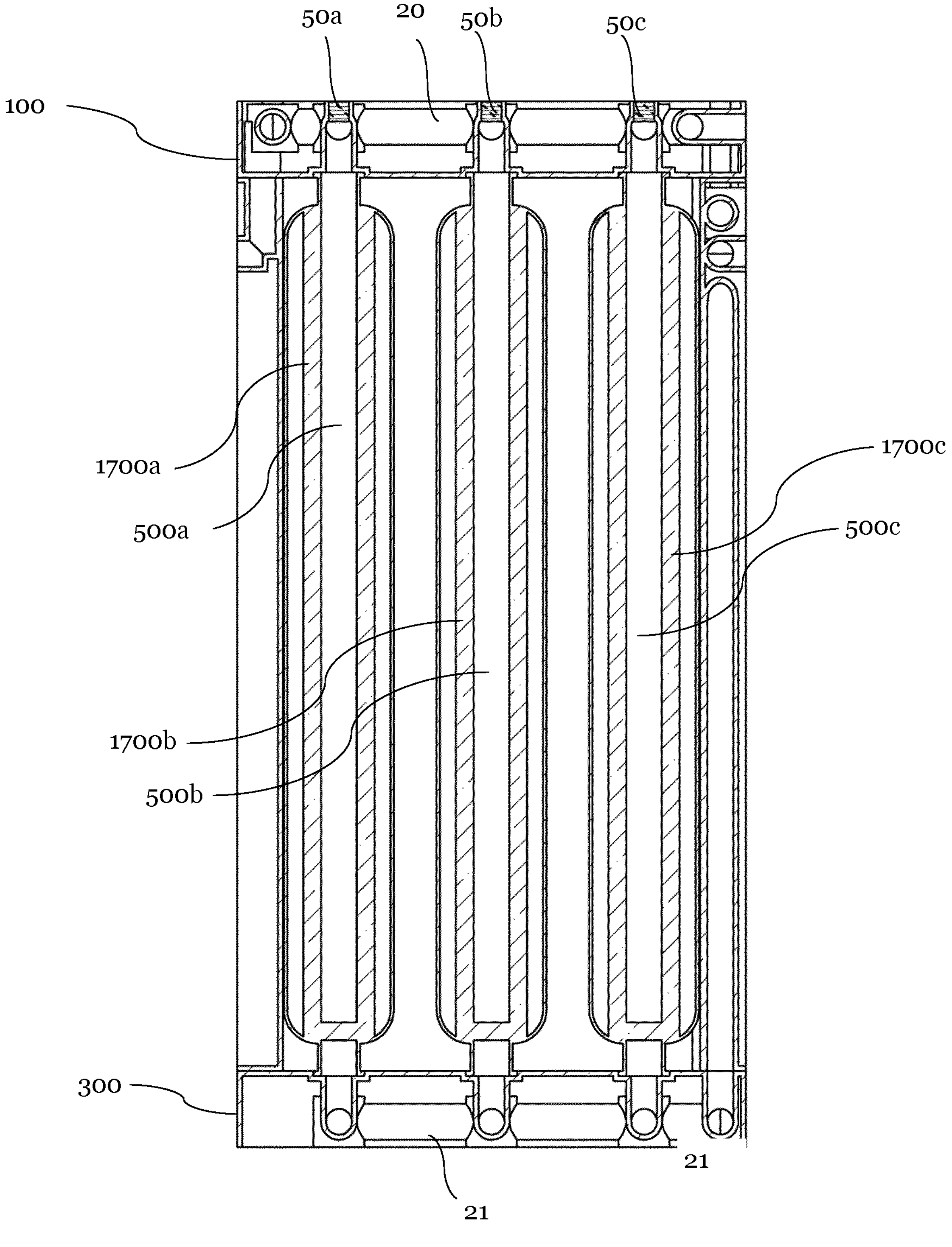
FIG. 17 schematically shows a further smart tank.

FIG. 17 schematically shows a further smart tank in a cut view. This may be the smart tank of FIGS. 16A and 16B. The smart tank comprises filter cartridges 1700*a*, 1700*b*, 1700*c*, such as a hollow fibre filter means. The filter cartridges are sidewall elements and each of the filter cartridges forms with the top plate element 100 and the bottom plate element 300 a respective reservoir 500*a*, 500*b*, 500*c*. Each of the filter cartridges 1700*a*, 1700*b*, 1700*c* includes a filter 1740*a*, 1740*b*, 1740*c*, that divides the respective reservoir in a filtrate side and a permeate side.

The filter cartridges 1700*a*, 1700*b*, 1700*c* are connected via a channel network 1270, comprising multiple channels 20, 21 and valves 50*a*, 50*b*, Soc. The channels and valves are arranged so that medium can be transferred to the filter cartridges 1700*a*, 1700*b*, 1700*c* serially or parallelly. In particular, by choosing respective positions of the valves of the channel network 1270 the flow of the medium can be guided through the filter cartridges 1700*a*, 1700*b*, 1700*c* as required. Further, the channel network and corresponding valves allow to provide integrity testing of each of the filter cartridges.

Figure 18:
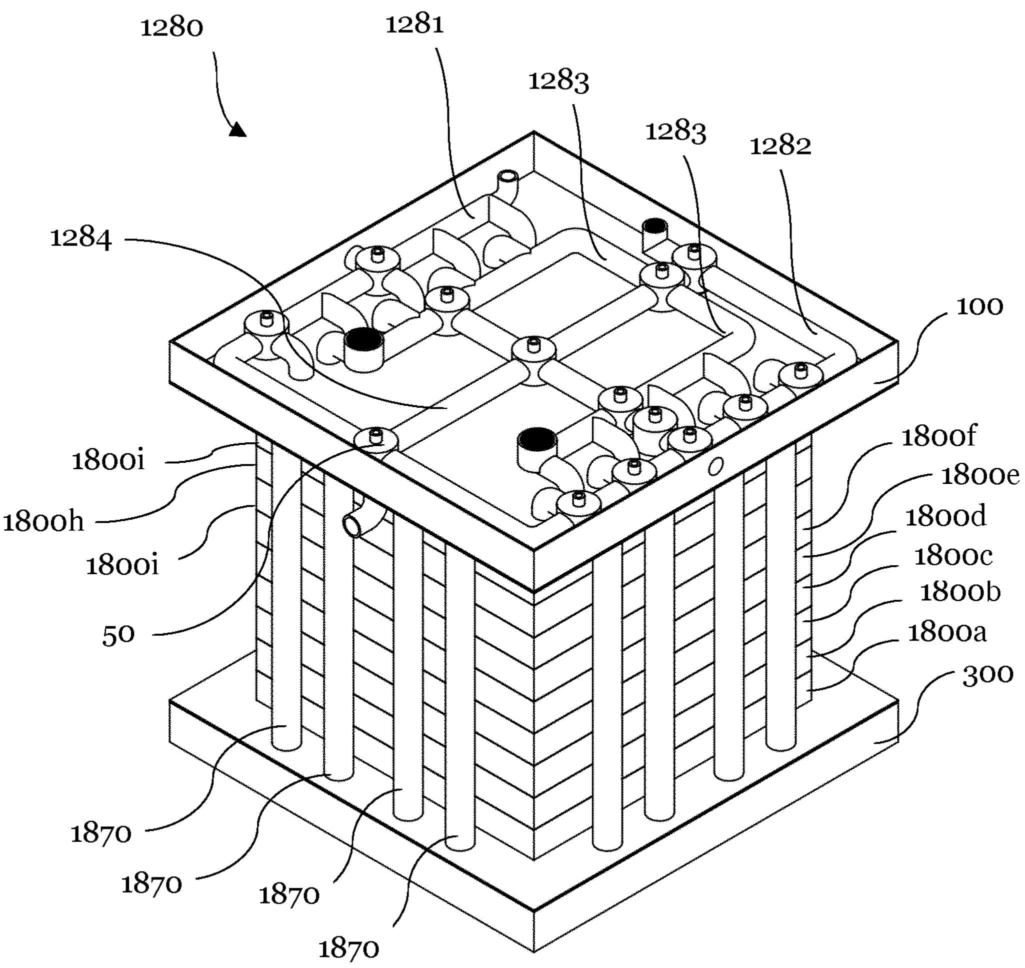
FIG. 18 schematically shows a further smart tank.

FIG. 18 schematically shows an even further smart tank comprising multiple crossflow cassettes 1800*a* to 1800*i*. The crossflow cassettes 1800*a* to 1800*i* are stacked and serve as sidewall elements. Together with the top plate element 100 and the bottom plate element 300 a reservoir is formed. Additionally, top plate element 100 and bottom plate element 300 are connected via press rods 1870 that allow to press the top plate element 100 and bottom plate element 300 as well as the sandwiched crossflow cassettes 1800*a* to 1800*i* together to provide a tight reservoir. The press rods 1870 may be threaded rods.

The smart tank comprises a channel network 1280, comprising input channels 1281, retentate channels 1282 and permeate channels 1283. Additionally, a waste channel 1284 may be provided. Further, valves 50 are provided. The valves can be controlled, so that permeate and/or retentate can be removed from the smart tank. Further, by controlling the valves and the pressure inside the tank, an integrity test can be performed, or the crossflow cassettes can flushed, e.g. by providing a buffer solution. Single aspects of the smart tank elements, smart tanks and smart tanks systems described above, can be combined to form further smart tank elements, smart tanks and smart tanks systems having combined functionalities.

Figure 19:
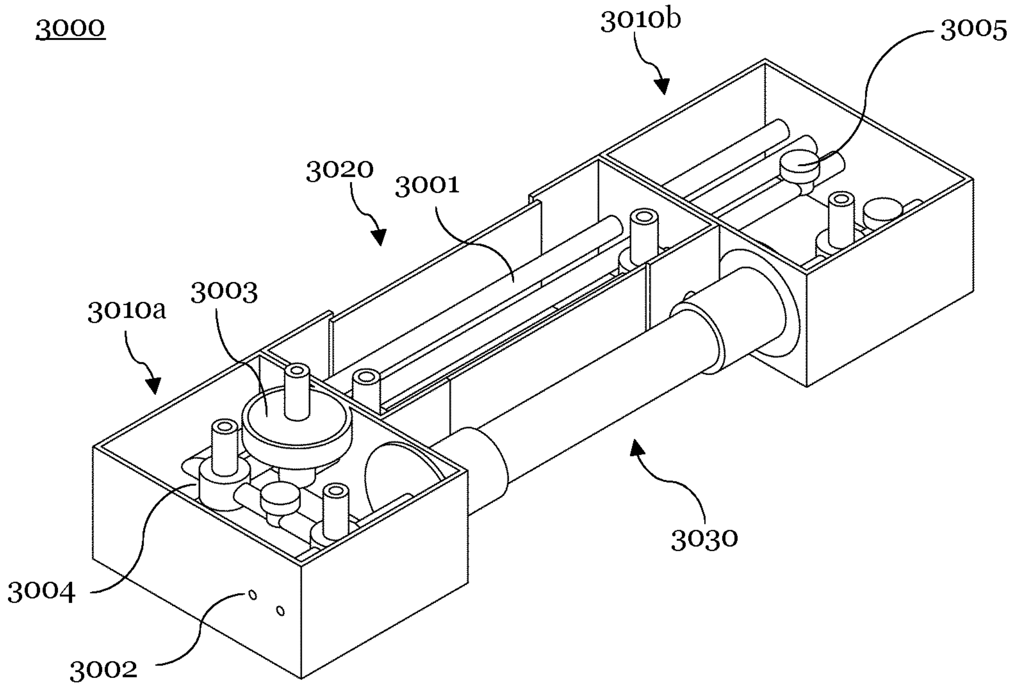
FIG. 19 schematically shows an adapter.
Figure 20:
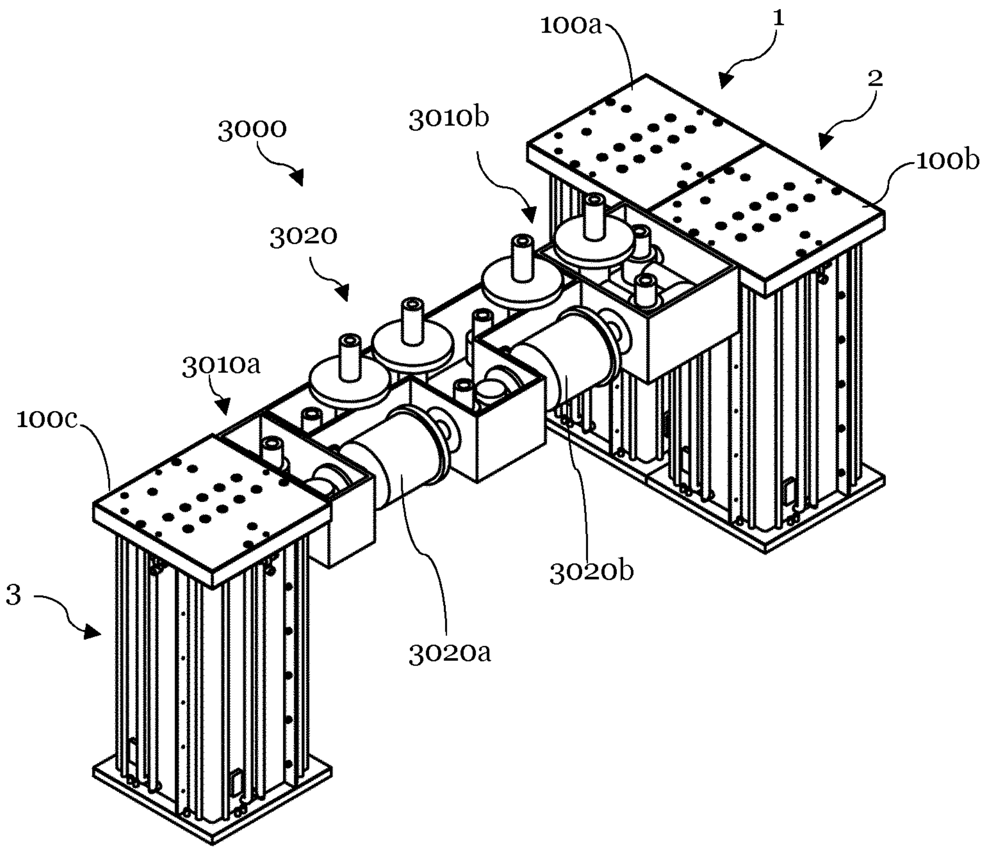
FIG. 20 schematically shows a smart tank system, wherein a further adapter is connected to three smart tanks

FIG. 19 schematically shows an adapter 3000 which may interconnect at least two smart tanks (as e.g. shown in FIG. 20). The adapter 3000 comprises at least one channel 3001 guiding at least one of a biochemical medium and/or an operating medium. The at least one channel 3001 may be further configured as described above with reference to the smart tank (cf. also embodiment 3, below).

Further, the depicted adapter 3000 comprises a fluidic module 3030. In the embodiment depicted in FIG. 19, the fluidic module 3030 is a hollow fiber filter. In further embodiments the adapter 3000 can comprise at least one (i.e. also multiple) fluidic module(s) 3030. The at least one fluidic module 3030 may be at least one of the following: a crossflow cassette, a crossflow hollow fiber module, a hollow fiber filter, a resin capsule, a filter capsule, and/or a magnetic tube. It is to be understood, that the adapter may include multiple fluidic modules of the same type and/or of different types. Further, it is to be understood, that the at least one channel 3001 may be at least partially arranged in the at least one fluidic module 3030, in particular in a capsule of the fluidic module.

Further, the at least one fluidic module 3030 may be replaceable. Thus, maintenance may be facilitated. Particularly, the at least one fluidic module 3030 may be replaceable by another type of fluidic module 3030. Thus, the functionality of the adapter 3000 may be adapted with reduced effort. Further, the at least one fluidic module may be replaceable by the same type of fluidic module. Thus, e.g. a consumed filter can be easily replaced.

Moreover, as illustrated in FIG. 19, the adapter 3000 comprises a port 3002, a filter 3003, a valve 3004 and a sensor 3005. In further embodiments, the adapter may comprise at least one (i.e. also multiple) of the following: a port 3002, a filter 3003, a valve 3004, a sensor 3005 and/or any other kind of operating means. Said operating means (port 3002, filter 3003, valve 3004 and sensor 3005) may be further configured as already described with reference to the smart tank. Moreover, said at least one port 3002 may be adapted to be connectable to at least one corresponding port of at least one smart tank and/or another adapter. Further, the adapter may be adapted to allow a horizontal and/or vertical arrangement of the adapter relative to a horizontal base surface. Particularly, the at least one port 3002 may be adapted to allow a vertical arrangement of the adapter relative to a horizontal base surface. Particularly, at least two ports may be configured to allow a connection of the top plate element of a first smart tank to the bottom plate element of a second smart tank by means of the adapter.

The adapter 3000 shown in FIG. 19 comprises three adapter units, a first side adapter unit 3010*a*, a second side adapter unit 3010*b* and a middle adapter unit 3020. The middle adapter unit 3020 is arranged between the first and second side adapter units 3010*a*, 3010*b*. Said adapter units may be connected by means of click connections.

Thus, the adapter units may be separate adapter units and interconnectable to form the adapter. Further, the at least two adapter units (or all adapter units) forming the adapter may be integrally formed. In further embodiments, the number of side adapter units and/or middle adapter units may be different. For example, the length of the adapter and/or the number of fluidic modules may be adjustable by choosing the number of side and/or middle adapter units.

The adapter 3000 may have a telescopic functionality and/or may be provided in different sizes. Preferably, the telescopic functionality is provided by the middle adapter unit 3020. This may be beneficial to adapt the distance between the side adapter units 3010. Thus, the adapter may be adapted to fluidic modules 3030 with different lengths. Thus, the flexibility of the adapter 3000 may be increased.

FIG. 20 schematically shows an adapter 3000 which is connected to three smart tanks 1, 2, 3. The adapter 3000 comprises two fluidic modules 3020*a*, 3020*b*. In the embodiment depicted in FIG. 20, the two fluidic modules 3020*a*, 3020*b* are filters, each comprising a capsule. The connection of the smart tanks 1, 2, 3 to the fluidic modules 3020*a*, 3020*b* is achieved by means of the adapter 3000, particularly via at least one of the first side adapter unit, the second side adapter unit and/or the middle adapter unit.

In FIG. 20, the adapter is attached to the top plate elements 100*a*, 100*b*, 100*c* of the smart tanks 1, 2, 3. In further embodiments, the adapter 3000 may be attached to the top plate element, the at least one sidewall element and/or the bottom plate element of a respective smart tank.

Further, the at least one adapter may allow an integrity test as already described with respect to the smart tank, above. Moreover, assembly, operation, fluidic connection and/or disassembly of the adapter with the at least one smart tank may be performed manually and/or with the aid of a respective handling manipulator. It is to be understood that assembly, operation, fluidic connection and/or disassembly of the at least one smart tank with at least one further smart tank may be performed manually and/or with the aid of a respective handling manipulator.

FURTHER EMBODIMENTS

Embodiment 1: A smart tank 1 for a bio-pharma process line, the smart tank comprising:

- a top plate element 100, at least one sidewall element 200, 210, 220, and a bottom plate element 300, wherein
- the top plate element, the at least one sidewall element and the bottom plate element are arranged to form at least one reservoir 500 for receiving at least one biochemical medium;
- the smart tank 1 comprises further
- at least one channel 20, 21, 22, 23, for guiding the at least one biochemical medium and/or an operating medium, wherein the at least one channel extends within at least one of the top plate element, the at least one sidewall element and/or the bottom plate element.

Embodiment 2: The smart tank 1 of embodiment 1, wherein the at least one channel 20, 21, 22, 23 extends in the at least one sidewall element 200, 210, 220 and at least one of the top plate element 100 and the bottom plate element 300.

Embodiment 3: The smart tank 1 of any previous embodiment, wherein the at least one channel 20, 21, 22, 23 is chosen from a group of channel-types, comprising the following channel types:

- an inlet channel, for guiding a biochemical medium and/or an operating medium to the reservoir of the smart tank, wherein the inlet channel may comprise a sparger;
- an outlet channel, for removing a biochemical medium and/or an operating medium from the reservoir of the smart tank;
- a retentate channel;
- a bypass-channel, for guiding a biochemical medium and/or an operating medium, wherein the bypass-channel is not connected to the reservoir of the smart tank, or wherein the bypass-channel is adapted to be fluidically separated from or connected to the reservoir of the smart tank;
- a heating or cooling channel for guiding a tempered heating or cooling medium;
- a sampling channel, for taking a sample of biochemical medium and/or of operating medium from the reservoir of the smart tank,
- a recirculation channel, for recirculating a medium in the smart tank,
- a wetting channel and/or flushing fluid channel for wetting or flushing components of the smart tank, particularly at least one filter,
- a product channel, for removing products from the reservoir of the smart tank;
- a feed channel for providing medium to the reservoir of the smart tank;
- a permeate or filtrate channel for removing/recirculating permeate/filtrate from the reservoir of the smart tank;
- a waste channel for removing waste from the reservoir of the smart tank;
- a cell bleed channel for harvesting cells;
- a cell channel for suppling, removing and/or transferring cells;
- a pressure channel, for pressurizing at least portions of the smart tank;
- a washing channel, a cleaning channel and/or eluding channel for loading different solutions to the smart tank, particularly to cartridges for chromatography, and wherein the smart tank may comprise multiple channels of different channel-types and/or the same channel type.

Embodiment 4: The smart tank 1 of any previous embodiment, further comprising at least one port 30, 32, wherein the at least one port is associated with a respective channel 20, and wherein the port is chosen from a group of port-types, comprising the following port-types:

- a fluid inlet port;
- a gas inlet port;
- a fluid outlet port;
- a gas outlet port;
- a cell bleed port,
- a medium supply port,
- a medium remove port,
- an element-interconnecting port, and
- a tank-interconnecting port.

Embodiment 5: The smart tank 1 of any previous embodiment, wherein the smart tank comprises at least one filter 40, wherein the at least one port 30 may be covered by the at least one filter 40, and wherein the filter may be chosen from a group of filter-types, comprising the following filter-types:

- a pre-filter;
- a sterile filter;
- a bacterial filter;
- a viral filter;
- a *Mycoplasma* filter;
- an ultrafiltration filter;
- a diafiltration filter;
- a cell filter;
- a cell harvest filter;
- a fluid filter;
- an air filter, and
- a gas filter, wherein the filter covering the at least one port may be heated and/or cooled.

Embodiment 6: The smart tank 1 of any previous embodiment, further comprising at least one valve 50, the at least one valve being associated with the at least one channel 20, wherein the valve may be a flow control valve, a cutoff valve, a pressure relief valve or a non-return valve, and wherein the valve may be a mechanical valve that is configured to be actuatable from the outside of the smart tank, by means of an actuating means 52.

Embodiment 7: The smart tank 1 of any previous embodiment, further comprising an adaptor plate element 600, wherein the adaptor plate element 600 is mounted on the top plate element 100, and wherein the adaptor plate element 600 is configured to cover a filter 40 and/or a port 30 at least partially, and/or wherein the adaptor plate element 600 is configured to support an actuating means 52 of a valve 50.

Embodiment 8: The smart tank 1 of any previous embodiment, further comprising at least one connector means 60, 62 for interconnecting the smart tank 1 with a further smart tank 2, wherein the connector means 60, 62 may provide a fluidical connection and may further be adapted for interconnecting the smart tank fluidically with a further smart tank without using a hose.

Embodiment 9: The smart tank 1 of the previous embodiment, wherein the connector means 60, 62 is a latching connector means, wherein the smart tank comprises a first latching connector means for directly interconnecting the smart tank with a further smart tank, which comprises a corresponding latching connector means, and/or wherein the smart tank comprises a second latching connector means, which is configured to latch with an inter-latching connector means 64, that is adapted to latch with a second latching connector means 62 of a further smart tank 2, so that the smart tank 1 can be directly interconnected with said further smart tank 2, via the inter-latching connector means 64.

Embodiment 10: The smart tank 1 of any previous embodiment, wherein the top plate element 100, the at least one sidewall element 200, 210, 220 and/or the bottom plate element 300 is formed from a plastic material, in particular by injection moulding or thermoforming, wherein top plate element, the sidewall element and/or the bottom plate element may be assembled from different sub-elements.

Embodiment 11: The smart tank 1 of any previous embodiment, wherein the inner surface 510 of the reservoir 500 and/or the at least one channel 20 is coated, particularly with a glass-based coating.

Embodiment 12: The smart tank 1 of any previous embodiment, wherein the smart tank is sterilizable, by means of autoclaving, ETO gas, and/or gamma radiation, prior, during or after being assembled.

Embodiment 13: The smart tank 1 of any previous embodiment, wherein the top plate element 100, at least one of the sidewall elements 200, 210, 220 and/or the bottom plate element 300 comprises at least one assembly-connecting means 70 and/or at least one corresponding assembly-connecting means 72, wherein the assembly-connecting means 70 and the corresponding assembly-connecting means 72 are configured to engage with each other, so as to secure an assembly of at least two adjacent elements, chosen from the group of top plate element 100, one or more sidewall elements 200, 210, 220 and bottom plate element 300, wherein the engagement of the assembly-connecting means 70 and the corresponding assembly-connecting means 72 may be a self-retaining engagement.

Embodiment 14: The smart tank 1 of any previous embodiment, wherein the smart tank comprises multiple side-wall elements 200, 210, 220, wherein the top plate element 100, the sidewall elements 200, 210, 220 and the bottom plate element 300 are arranged to form the reservoir 500, wherein at least one of the sidewall elements 200, 210, 220 and in particular each one of the multiple sidewall elements 200, 210, 220 comprises a first sidewall portion **200*a* and a second sidewall portion 200*b*, wherein the first sidewall portion 200*a* and the second sidewall portion 200*b* enclose an angle $\alpha$, wherein the angle $\alpha$ is about 90° or about 120° or about 135°, so that the reservoir 500 has a substantial rectangular, hexagonal or octagonal cross-section, when seen from the top plate element side, wherein the first sidewall portion 200*a* may extend laterally farther than the second sidewall portion 200*b***, and wherein the inner edge formed by the first sidewall portion and the second sidewall portion, may be a rounded edge.

Embodiment 15: The smart tank 1 of any previous embodiment, wherein the at least one the sidewall element 200, 210, 220 and in particular each one of the sidewall elements 200, 210, 220 is a curved sidewall element when seen from the top plate element side, so that the reservoir 500 has a substantial circular or oval cross-section, when seen from the top plate element side.

Embodiment 16: The smart tank 1 of any previous embodiment, wherein any one of the top plate element 100, the at least one sidewall element 200, 210, 220 and/or the bottom plate element 300 comprises at least one first channel portion **20*a* and a at least one channel-connecting means 80 being associated with a respective first channel portion 20*a*, and wherein a different one of the top plate element 100, the at least one sidewall element 200, 210, 220, a further side wall element 200, 210, 220 and/or the bottom plate element 300 comprises at least one second channel portion 20*b* and a at least one corresponding channel-connecting means 82 being associated with a respective second channel portion 20*b*, wherein the channel-connecting means 80 and the corresponding channel-connecting means 82 are configured to engage with each other, so as to form a fluidically sealed channel connection, between the first channel portion 20*a* and the second channel portion 20*b*, so as to form the at least one channel 20**.

Embodiment 17: The smart tank 1 of any previous embodiment, wherein the smart tank further comprises at least one of the following:

a pumping means, wherein the pumping means may be separated from the reservoir and/or the at least one channel by a flexible membrane, so as to prevent direct contact between the at least one biochemical medium and the pumping means;

a stirring means 90, wherein the stirring means may be driveable from the outside of the smart tank;

a blending means, such as a fluid deflection plate, which may be integrally formed with either one of the side-wall elements, the top plate element and/or the bottom plate element;

a cell-harvest-means;

at least one cartridge for chromatography **1500*a*, 1500*b*, 1500*c***;

a cross-flow-cassette;

a filter cartridge 1400*a*, 1400*b*, 1400*c*,
a resin means,
a hollow-fibre means 1700*a*, 1700*b*, 1700*c*;
a rupture disc and/or
a bag, wherein the bag may line the inner wall of the reservoir.

Embodiment 18: The smart tank 1 of any previous embodiment, wherein the smart tank is connectable to at least one sensor 1010 or a sensor module 1000, comprising multiple sensors 1010, wherein the at least one sensor and the sensors of the sensor module are chosen from the group of pH sensor,
temperature sensor,
dissolved oxygen sensor,
biomass sensor,
foam sensor,
pressure sensor,
flow sensor,
O2 sensor,
N2 sensor,
CO2 sensor, and
spectroscopy means, such as RAMAN, NIR and/or UV spectroscopy means.

Embodiment 19: Smart tank assembly 1' adapted to be assembled to a smart tank 1 according to any one of embodiments 1 to 18, wherein the smart tank assembly 1' comprises a top plate element 100, at least one sidewall element 200, 210, 220, and a bottom plate element 300, wherein
the top plate element 100, the at least one sidewall element 200, 210, 220 and the bottom plate element 300 can be assembled to form a reservoir 500 for receiving at least one biochemical medium, wherein
at least one of the top plate element 100, the at least one sidewall element 200, 210, 220 and the bottom plate element 300 comprises
at least one channel 20, for guiding the at least one biochemical medium and/or an operating medium.

Embodiment 20: A smart tank system, comprising multiple smart tanks 1, 2, 3, according to any one of the previous embodiments 1 to 18, wherein a first smart tank 1 is interconnectable with a second smart tank 2 by at least one connector means 60, when the second smart tank 2 is arranged directly adjacent to the first smart tank 1, and wherein
at least one of the one or more channels 20, 21, 22 of the first smart tank 1 is fluidically connected to a respective channel of the second smart tank 2, when the first smart tank is interconnected with the second smart tank 2.

Embodiment 21: The smart tank system according to embodiment 20, wherein a height dimension of the first smart tank 1 is smaller than a height dimension of the second smart tank 2, and wherein
the smart tank system comprises at least one height compensation means 1100, 1102 that is adapted to be coupled to the first smart tank 1, so that the top plate element 100 of the first smart tank 1 is installed in substantially the same height as the top plate element 102 of the second smart tank 2, when the height compensation means 1100, 1102 is coupled to the first smart tank 1.

Embodiment 22: The smart tank system according to any one of embodiments 20 or 21, wherein a volume of the first smart tank 1 is smaller than a volume of the second smart tank 2, wherein the first smart tank is adapted to be installed on top of the second smart tank.

Embodiment 23: A method 2000 for assembling a smart tank 1 according to any one of embodiments 1 to 18, wherein the method comprises the following steps:

providing 2100 a top plate element;
providing 2200 at least one sidewall element;
providing 2300 a bottom plate element;
assembling 2400 the top plate element, at least one sidewall element, and a bottom plate element to form a reservoir for receiving at least one biochemical medium.

The invention claimed is:

1. A smart tank (1) for a bio-pharma process line, the smart tank comprising:

a top plate element (100), at least one sidewall element (200, 210, 220), and a bottom plate element (300), wherein
the top plate element, the at least one sidewall element and the bottom plate element are arranged to form at least one reservoir (500) for receiving at least one biochemical medium; and
the smart tank (1) comprises further
at least one integrated channel (20, 21, 22, 23), for guiding the at least one biochemical medium and/or an operating medium, wherein the at least one integrated channel extends within the top plate element and at least one of the at least one sidewall element and/or the bottom plate element, wherein the integrated channel is fluidly connected to the at least one reservoir and is configured to guide at least one process medium from or to the reservoir, wherein the length of the at least one integrated channel is longer than the thickness of the respective top plate element, sidewall element and/or the bottom plate element, wherein
an one of the to plate element (100), the at least one sidewall element (200, 210, 220) and/or the bottom plate element (300) comprises at least one first channel portion (20*a*) and at least one channel-connecting means (80) being associated with a respective first channel portion (20*a*), and wherein
a different one of the to late element (100) the at least one sidewall element 200, 210, 220), a further side wall element (200, 210, 220) and/or the bottom plate element (300) comprises at least one second channel portion 20 and at least one corresponding channel-connecting means (82) being associated with a respective second channel portion (20*b*), wherein
the channel-connecting means (80) and the corresponding channel-connecting means (82) are configured to engage with each other, so as to form a fluidically sealed channel connection between the first channel portion (20*a*) and the second channel portion (20*b*), so as to form the at least one integrated channel (20).

2. The smart tank (1) of claim 1, wherein the at least one integrated channel (20, 21, 22, 23) is chosen from a group of channel-types, consisting of the following channel types:

an inlet channel, for guiding a biochemical medium and/or an operating medium to the reservoir of the smart tank, wherein the inlet channel comprises a sparger;
an outlet channel, for removing a biochemical medium and/or an operating medium from the reservoir of the smart tank;
a retentate channel;

a bypass-channel, for guiding a biochemical medium and/or an operating medium, wherein the bypass-channel is adapted to be fluidically separated from or connected to the reservoir of the smart tank;

a heating or cooling channel for guiding a tempered heating or cooling medium;

a sampling channel, for taking a sample of biochemical medium and/or of operating medium from the reservoir of the smart tank;

a recirculation channel, for recirculating a medium in the smart tank;

a wetting channel and/or flushing fluid channel for wetting or flushing components of the smart tank comprising at least one filter;

a product channel, for removing products from the reservoir of the smart tank;

a feed channel for providing medium to the reservoir of the smart tank;

a permeate or filtrate channel for removing/recirculating permeate/filtrate from the reservoir of the smart tank;

a waste channel for removing waste from the reservoir of the smart tank;

a cell bleed channel for harvesting cells;

a cell channel for suppling, removing and/or transferring cells;

a pressure channel, for pressurizing at least portions of the smart tank; and a washing channel, a cleaning channel and/or eluding channel for loading different solutions to the smart tank comprising cartridges for chromatography, and wherein the smart tank comprises multiple channels of different channel-types and/or the same channel type.

3. The smart tank (1) of claim 1, further comprising at least one port (30, 32), wherein the at least one port is associated with a respective integrated channel (20), and wherein the port is chosen from a group of port-types, consisting of the following port-types:

a fluid inlet port;

a gas inlet port;

a fluid outlet port;

a gas outlet port;

a cell bleed port, a cell transfer port, a medium supply port, a medium remove port, an element-interconnecting port, and a tank-interconnecting port.

4. The smart tank (1) of claim 1, wherein the smart tank further comprises at least one filter (40), at least one port (30) covered by the at least one filter (40), and wherein the filter is chosen from a group of filter-types, consisting of the following filter-types:

a pre-filter;

a sterile filter;

a bacterial filter;

a viral filter;

a *Mycoplasma* filter;

an ultrafiltration filter;

a diafiltration filter;

a cell filter;

a cell harvest filter;

a fluid filter;

an air filter, and a gas filter, wherein the filter covering the at least one port is heated and/or cooled.

5. The smart tank (1) of claim 1, further comprising at least one valve (50), the at least one valve being associated with the at least one integrated channel (20), wherein the valve is a flow control valve, a cutoff valve, a pressure relief valve or a non return valve, and wherein the valve is a mechanical valve that is configured to be actuatable from the outside of the smart tank, by means of an actuating means (52).

6. The smart tank (1) of claim 1, further comprising at least one connector means (60, 62) for interconnecting the smart tank (1) with a further smart tank (2), wherein the connector means (60, 62) provides a fluidical connection and is further adapted for interconnecting the smart tank fluidically with a further smart tank without using a hose.

7. The smart tank (1) of claim 1, wherein an inner surface (510) of the reservoir (500) and/or the at least one integrated channel (20) is coated, with a glass-based coating and/or wherein the smart tank is sterilizable, by means of autoclaving, ETO gas, and/or gamma radiation, prior, during or after being assembled.

8. The smart tank (1) of claim 1, wherein the top plate element (100), the at least one sidewall element (200, 210, 220) and/or the bottom plate element (300) comprises at least one assembly-connecting means (70) and/or at least one corresponding assembly-connecting means (72) configured to secure an assembly of at least two adjacent elements, chosen from the group of top plate element (100), the at least one sidewall element (200, 210, 220) and bottom plate element (300), wherein engagement of the assembly-connecting means (70) and the corresponding assembly-connecting means (72) is a self-retaining engagement.

9. The smart tank (1) of claim 1, wherein the smart tank comprises multiple sidewall elements (200, 210, 220), wherein the top plate element (100), the sidewall elements (200, 210, 220) and the bottom plate element (300) are arranged to form the at least one reservoir (500), wherein each of the multiple sidewall elements (200, 210, 220) comprises a first sidewall portion (200*a*) and a second sidewall portion (200*b*), wherein the first sidewall portion (200*a*) and the second sidewall portion (200*b*) enclose an angle $\alpha$, wherein the angle $\alpha$ is about 90° or about 120° or about 135°, so that the at least one reservoir (500) has a rectangular, hexagonal or octagonal cross-section, when seen from the top plate element side, wherein the first sidewall portion (200*a*) extends laterally farther than the second sidewall portion (200*b*), and wherein an inner edge formed by the first sidewall portion and the second sidewall portion, is a rounded edge and.

10. The smart tank (1) of claim 1, wherein the smart tank further comprises at least one of the following:

a pumping means, wherein the pumping means is separated from the reservoir and/or the at least one integrated channel by a flexible membrane, so as to prevent direct contact between the at least one biochemical medium and the pumping means;

a stirring means (90), wherein the stirring means is driveable from the outside of the smart tank;

a blending means comprising a fluid deflection plate, which is integrally formed with either one of the at least one sidewall element, the top plate element and/or the bottom plate element;

a cell-harvest-means;

at least one cartridge for chromatography (1500*a*, 1500*b*, 1500*c*);
a cross-flow-cassette;
a filter cartridge (1400*a*, 1400*b*, 1400*c*),
a resin means,
a hollow-fibre means (1700*a*, 1700*b*, 1700*c*);
a rupture disc and/or
a bag, wherein the bag lines the inner wall of the reservoir and/or, wherein the smart tank is connectable to at least one sensor (1010) or a sensor module (1000), comprising multiple sensors (1010), wherein the at least one sensor and the sensors of the sensor module are chosen from the group of
pH sensor,
temperature sensor,
dissolved oxygen sensor,
biomass sensor,
foam sensor,
pressure sensor,
flow sensor,
$O_2$ sensor,
$N_2$ sensor,
$CO_2$ sensor, and
spectroscopy means, comprising RAMAN, NIR and/or UV spectroscopy means.

11. The smart tank (1) of claim 1, wherein at least one of the top plate element, the at least one sidewall element, and the bottom plate element, or at least a sub-element thereof, in which a portion of the at least one integrated channel extends, is formed by 3D printing.

12. A smart tank system, comprising multiple smart tanks (1, 2, 3), wherein the smart tank system comprises:
a first smart tank (1) according to claim 1 that is interconnectable with a second smart tank (2) according to claim 1 by at least one connector means (60), when the second smart tank (2) is arranged directly adjacent to the first smart tank (1), and wherein
at least one of the one or more integrated channels (20, 21, 22) of the first smart tank (1) is fluidically connected to a respective integrated channel of the second smart tank (2), when the first smart tank is interconnected with the second smart tank (2).

13. The smart tank system according to claim 12 further comprising:
an adapter (3000), wherein the adapter (3000) is adapted to interconnect the first smart tank (1) and the second smart tank (2), wherein
the adapter (3000) includes at least one integrated channel (3001) and at least one fluidic module (3030), wherein
the at least one integrated channel (3001) of the adapter (3000) is fluidically connected to a respective integrated channel of the first smart tank (1) and a respective integrated channel of the second smart tank (2), when the adapter (3000) interconnects the first smart tank (1) and the second smart tank (2), and wherein
the at least one fluidic module (3030) is at least one of the following:
a crossflow cassette,
a crossflow hollow fiber module,
a hollow fiber filter,
a resin capsule,
a filter capsule, and/or
a magnetic tube.

14. The smart tank system according to claim 12, wherein
a height dimension of the first smart tank (1) is smaller than a height dimension of the second smart tank (2), and wherein
the smart tank system comprises at least one height compensation means (1100, 1102) that is adapted to be coupled to the first smart tank (1), so that the top plate element (100) of the first smart tank (1) is installed in substantially the same height as the top plate element (102) of the second smart tank (2), when the height compensation means (1100, 1102) is coupled to the first smart tank (1), and/or wherein
a volume of the first smart tank (1) is smaller than a volume of the second smart tank, wherein the first smart tank is adapted to be installed on top of the second smart tank.

15. A method (2000) for assembling a smart tank (1) according to claim 1, wherein the method comprises the following steps:
providing (2100) a top plate element;
providing (2200) at least one sidewall element;
providing (2300) a bottom plate element;
assembling (2400) the top plate element, the at least one sidewall element, and the bottom plate element to form a reservoir for receiving at least one biochemical medium.

16. A smart tank (1) for a bio-pharma process line, the smart tank comprising:
a top plate element (100), at least one sidewall element (200, 210, 220), and a bottom plate element (300), wherein
the top plate element, the at least one sidewall element and the bottom plate element are arranged to form at least one reservoir (500) for receiving at least one biochemical medium; and
the smart tank (1) comprises further
at least one integrated channel (20, 21, 22, 23), for guiding the at least one biochemical medium and/or an operating medium, wherein the at least one integrated channel extends within the top plate element and at least one of the at least one sidewall element and/or the bottom plate element, wherein the integrated channel is fluidly connected to the at least one reservoir and is configured to guide at least one process medium from or to the reservoir, wherein the length of the at least one integrated channel is longer than the thickness of the respective top plate element, sidewall element and/or the bottom plate element,
wherein the top plate element comprises at least one integrated valve (50), the at least one integrated valve being associated with the at least one integrated channel.

* * * * *